(12) United States Patent
Unsicker et al.

(10) Patent No.: US 6,790,824 B1
(45) Date of Patent: Sep. 14, 2004

(54) CYTOKINES HAVING NEUROTROPHIC ACTIVITY

(75) Inventors: Klaus Unsicker, Heidelberg (DE); Jens Pohl, Hambrücken (DE); Michael Paulista, Leimen (DE); Rolf Bechtold, Heidelberg (DE)

(73) Assignee: Biopharm Gesellschaft zur biotechnologischen Entwicklung von Pharmaka mbH, Heidelberg (DE)

( * ) Notice: Subject to any disclaimer, the term of this patent is extended or adjusted under 35 U.S.C. 154(b) by 0 days.

(21) Appl. No.: 09/527,275

(22) Filed: Mar. 17, 2000

Related U.S. Application Data

(63) Continuation of application No. PCT/EP98/06004, filed on Sep. 21, 1998.

(30) Foreign Application Priority Data

Sep. 19, 1997 (EP) .............................................. 97116373

(51) Int. Cl.[7] ........................ A01N 37/18; A61K 38/00; A61K 38/24; A61K 38/27
(52) U.S. Cl. .......................... 514/2; 530/350; 530/399; 424/85.1; 424/198.1
(58) Field of Search ............................ 424/85.1, 198.1; 514/2; 530/350, 399

(56) References Cited

FOREIGN PATENT DOCUMENTS

| EP | 105014 | | 4/1984 | | |
|---|---|---|---|---|---|
| EP | 0 454 400 A2 | | 10/1991 | | |
| WO | WO 9209607 | | 6/1992 | | |
| WO | WO 9711965 | | 4/1997 | | |
| WO | WO 9719694 | | 6/1997 | | |
| WO | WO-97/19694 | * | 6/1997 | .......... | A61K/38/18 |
| WO | WO 99/12560 | | 3/1999 | | |

OTHER PUBLICATIONS

Goulin et al., 1996, J.Neuroscience Research, 43, pp. 454–464.*
Poulsen et al., 1994, Neuron, 13, pp. 1245–1252.*
Kriegelstein et al., Distinct modulatory actions of TGF–b and LIF in neurotrophin–mediated survival of developing sensory neurons. Neurochem.Research, 21, No. 7, 1996, pp. 843–850.*
Krieglstein, K., and Unsicker, K., "Distinct Modulatory Actions of TGF–β and LIF on Neurotrophin–Mediated Survival of Developing Sensory Neurons," Neurochem. Res., 21(7):843–850 (1996).
Engele, J. and Bohn, M.C., "The Neurotrophic Effects of Fibroblast Growth Factors on Dopaminergic Neurons in vitro Are Mediated by Mesencephalic Glia," J. Neurosci. 11(10):3070–3078 (1991).

Stahl, N. and Yancopoulos, G.D., "The Tripartite CNTF Receptor Complex: Activation and Signaling Involves Components Shared with Other Cytokines," J. Neurobiol. 25:1454–1466 (1994).

Collins, F., "Developmental Time Course of the Effect of Nerve Growth Factor on the Parasympathetic Ciliary Ganglion," Dev. Brain Res. 39: 111–116 (1988).

Krieglstein, K., et al., "Trophic and Protective Effects of Growth/Differentiation Factor 5, a Member of the Transforming Growth Factor–β Superfamily, on Midbrain Dopaminergic Neurons," J. Neurosci. Res., 42:724–732 (1995).

Müller, T. H. and Unsicker, K., "High–Performance Liquid Chromatography With Electrochemical Detection as a Highly Efficient Tool For Studying Catecholaminergic Systems. I. Quantification of Noradrenaline, Adrenaline and Dopamine in Cultured Adrenal Medullary Cells," J. Neurosci. Methods 4:39–52 (1981).

Winkler, H., and Smith, A. D., "The Chromaffin Granule and the Storage of Catecholamines," Handbook of Physiology, 6(7):321–399.

Abe, M., et al., "An Assay for Transforming Growth Factor–β Using Cells Transfected with a Plasminogen Activator Inhibitor–1 Promoter–Luciferase Construct," Anal. Biochem 216:276–284 (1984).

Krieglstein, K., and Unsicker, K., "Proteins From Chromaffin Granules Promote Survival of Dorsal Root Ganglionic Neurons: Comparison With Neurotrophins," Dev. Brain. Res. 93:10–17 (1996).

Bottenstein, J. E., et al. "Selective Survival of Neurons From Chick Embryo Sensory Ganglionic Dissociates Utilizing Serum–Free Supplemented Medium," Exp. Cell Res. 125:183–190 (1980).

Arumäe, U., et al., "Neurotrophins and Their Receptors in Rat Peripheral Trigeminal System During Maxillary Nerve Growth," J. Cell Biol. 122(5):1053–1065 (1993).

Kerstin Krieglstein, et al., "Glial Cell Line–Derived Neurotrophic Factor Requires Transforming Growth Factorβ for Exerting Its Full Neurotrophic Potential on Peripheral and CNS Neurons," J Neurosci, 18(23):9822–9834.

* cited by examiner

Primary Examiner—John Ulm
Assistant Examiner—Olga N. Chernyshev
(74) Attorney, Agent, or Firm—Hamilton, Brook, Smith & Reynolds, P.C.

(57) ABSTRACT

The present invention relates to a pharmaceutical composition having neurotrophic activity, comprising a biologically active amount of at least two cytokines, wherein at least one of said cytokines is BMP, GDF, TGF–β or GDNF.

3 Claims, 22 Drawing Sheets

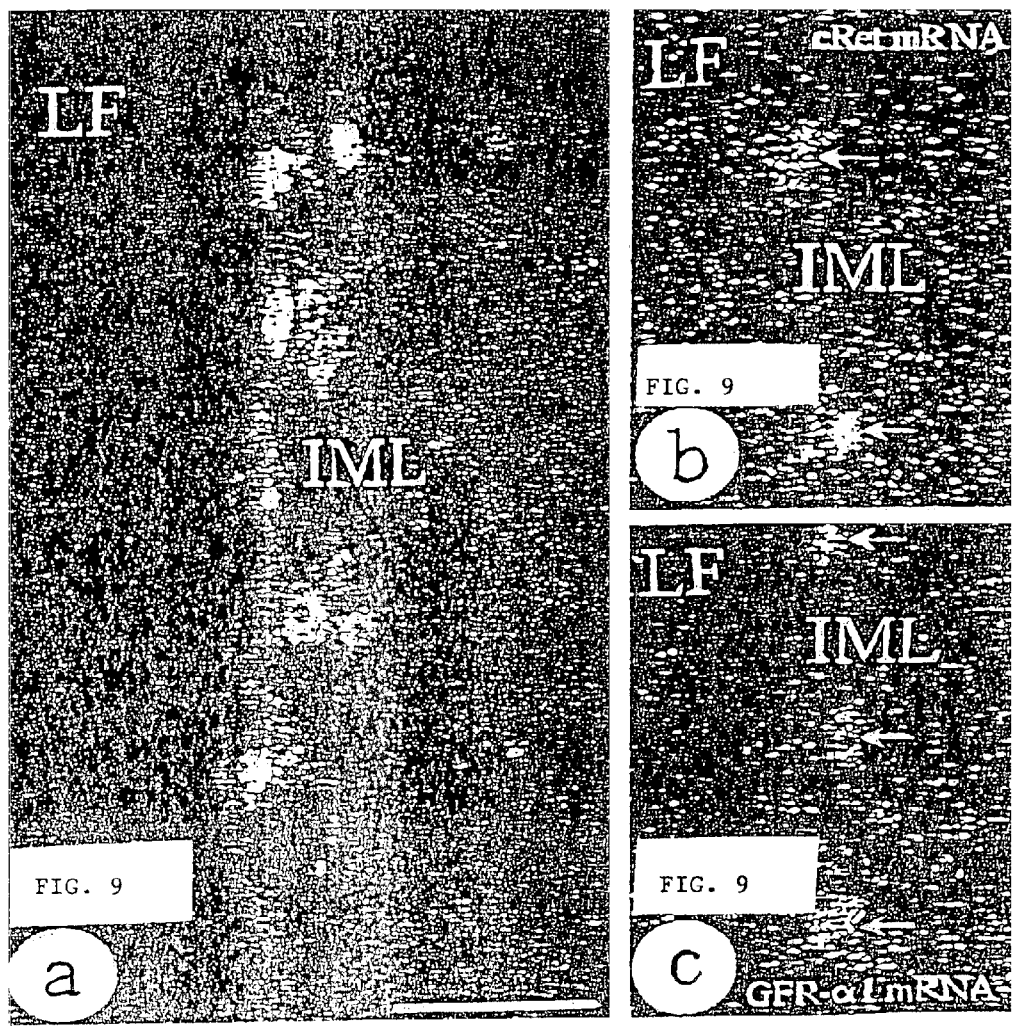

US 6,790,824 B1

CYTOKINES HAVING NEUROTROPHIC ACTIVITY

RELATED APPLICATION(S)

This application is a Continuation of PCT/EP98/06004 filed on Sep. 21, 1998, which designated the U.S., which claims priority to European Patent Application Number 97 116 373.8 filed on Sep. 19, 1997, the entire contents of which are incorporated herein by reference in their entirety.

BACKGROUND OF THE INVENTION

The present invention relates to a pharmaceutical composition having neurotrophic activity, for treating peripheral and/or CNS-disorders in mammals.

GDF-5 is a bone morpho genetic protein like molecule which, similar to other members of the transforming growth factor beta (TGF-β) superfamily, has been implicated in neurotrophic functions. For example, TGF-β1, -β2, and -β3, as well as activin A, bone morphogenetic proteins (BMP) -2, -4, -6, -7, -12, glial cell line-derived neurotrophic-like factors (GDNF-like), and GDF-5 have all been shown to promote in vitro the survival of midbrain dopaminergic neurons by various mechanisms. GDNF also acts on a wide spectrum of peripheral neurons.

The discovery of GDNF as a neurotrophic factor for midbrain dopaminergic neurons was a hallmark in the search for novel molecules that may have relevance in the treatment of neurodegenerative diseases, as e.g. Parkinson's disease. The significance of GDNF is further underscored by its efficacy in several animal models of PD including non-human primates, ubiquitous expression in neurons of the CNS, and its widening spectrum of responsive neuron populations. GDNF signals via the tyrosine kinase receptor c-ret in co-operativity with a GPI-linked α receptor, the GDNFRα. GDNF is a member of the TGF-β superfamily, its closest relatives being neurturin. Targeted mutations of the GDNF or c-Ret genes have indicated that GDNF is essentially required for the development of the kidney, major portions of the enteric nervous system and the sympathetic superior cervical ganglion. However, GDNF does not support the survival of most peripheral neurons in low-density dissociated cultures and defined media. Follow-up experiments in which GDNF has been shown to promote the survival of enriched peripheral autonomic and sensory neurons were all performed using serum throughout the whole culture period. Furthermore, the dopaminotrophic effect of GDNF was established in an extremely complex culture system where its most prominent effect did not become apparent until day 7 in culture.

TGF-βs are widely distributed and contextually acting cytokines with prominent roles in development and cell cycle control. TGF-βs have been implicated in the regulation of neuronal survival of e.g. motoneurons, sensory and midbrain dopaminergic neurons. It should be noted, however, that TGF-β shows no or marginal effects on highly enriched, serum-free neuron cultures, as e.g. sensory neurons.

Thus, the technical problem underlying the present invention is to provide a new system having improved neurotrophic activity, for the treatment of peripheral and/or CNS-disorders in mammals.

The solution to the above technical problem is achieved by the embodiments characterized in the claims.

In particular, the present invention relates to a pharmaceutical composition having a neurotrophic activity, comprising a biologically active amount of at least two cytokines or functionally active derivatives or parts thereof and optionally a pharmaceutically acceptable carrier and/or diluent, wherein at least one of said cytokines is BMP, GDF, TGF-β or GDNF. The term "BMP" includes BMP-2, BMP4, BMP-6, BMP-7, BMP-11 and BMP-12. The term "TGF-β" includes TGF-β1, TGF-β2 and TGF-β3. The term "GDNF" includes GDNF, neurturin and persephin. The terms "functionally active derivative" and "functionally active part" refer to a proteinous compound exhibiting at least part of the biological function of the respective cytokine. The cytokines used in the pharmaceutical composition according to the present invention may be selected from the group consisting of GDF such as GDF-5, GDF-6, GDF-7, GDF-8 and GDF-9, GDNF, TGF such as TGF-β or TGF-β, e.g. TGF-β1, TGF-β2 or TGF-β3, activin A, BMP such as BMP-2, BMP4, BMP6, BMP-7, BMP-11, BMP-12, BDNF, NGF, neurotrophines such as NT-3 or NT4, EGF, CNTF and FGF such as FGF-2.

Preferred embodiments of the present invention the pharmaceutical composition comprise the following combinations: GDF-5 and NGF or NT-3 or GDNF, TGF-β and GDNF or FGF-2 or CNTF or NT-3 or NGF, NGF and BMP-4 or BMP-12, NT-3 and BMP-2 or BMP-7 or BMP-12.

As a surprising fact, if at least one of BMP, GDF, TGF-β and GDNF is present in the above defined pharmaceutical composition, a synergistic effect can be observed resulting in an increased neurotrophic activity, as compared to e. g. known compositions without GDF and/or GNDF.

The pharmaceutical composition according to the present invention may be used for the treatment of peripheral and/or CNS-disorders in mammals, preferably in man, such as Parkinson's disease, Alzheimer's disease, ALS or other dementia, other neurodegenerative disorders of the central nervous system and peripheral neuropathies including diabetes, cisplatinium or other genetic or acquired peripheral nerve diseases.

Figure 1:
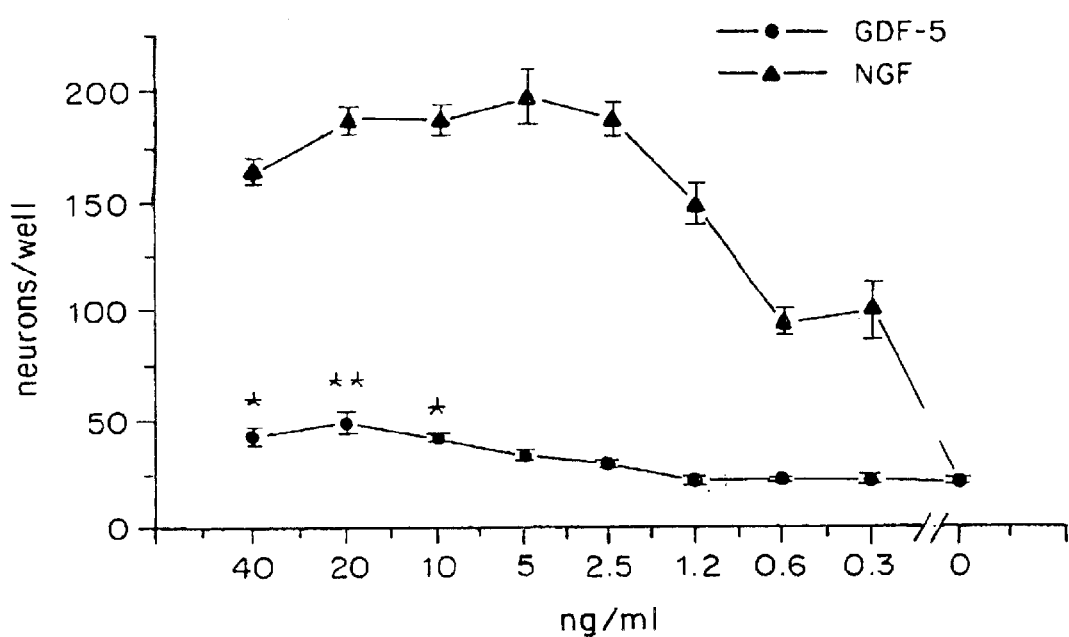
FIG. 1 depicts a comparison of dose-response curves of GDF-5 and NGF in cultures of E8 chick DRG. Data are shown as means±SEM from three independent experiments with triplicate cultures. *P<0.05; **P<0.01 significantly different from untreated negative control values.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 2A:
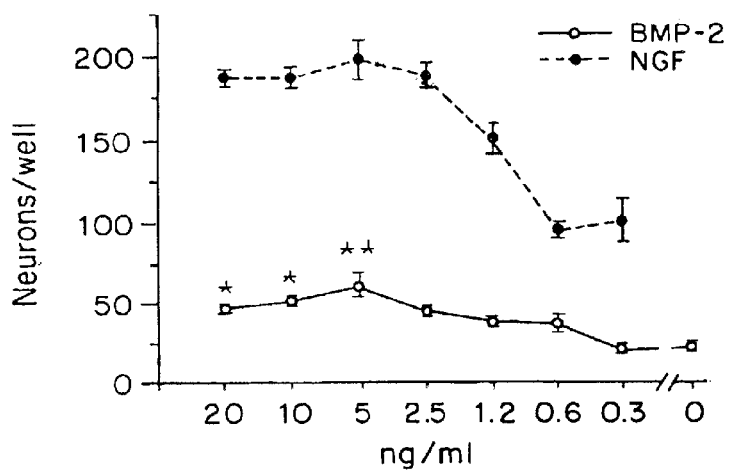
FIGS. 2A through 2F depict a same experiment as in FIG. 1 except that (2A) BMP-2, (2B) BMP4, (2C) BMP-6, (2D) BMP-7, (2E) BMP-11 and (2F) BMP-12 have been used in the respective composition.
Figure 2B:
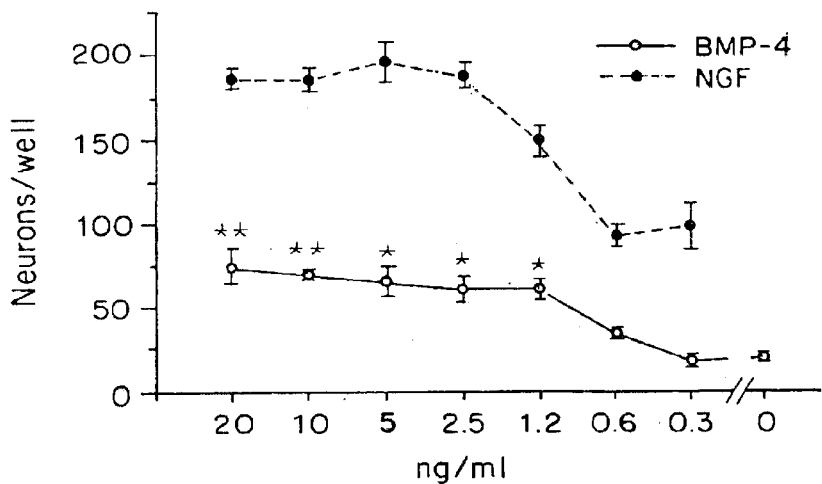
Figure 2C:
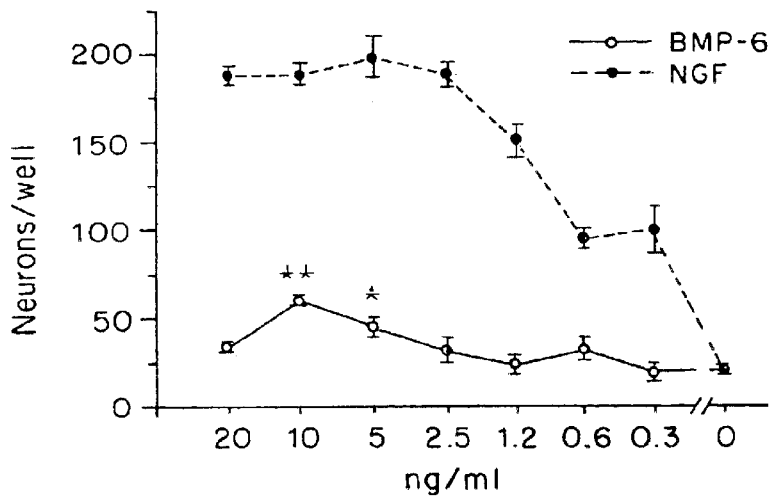
Figure 2D:
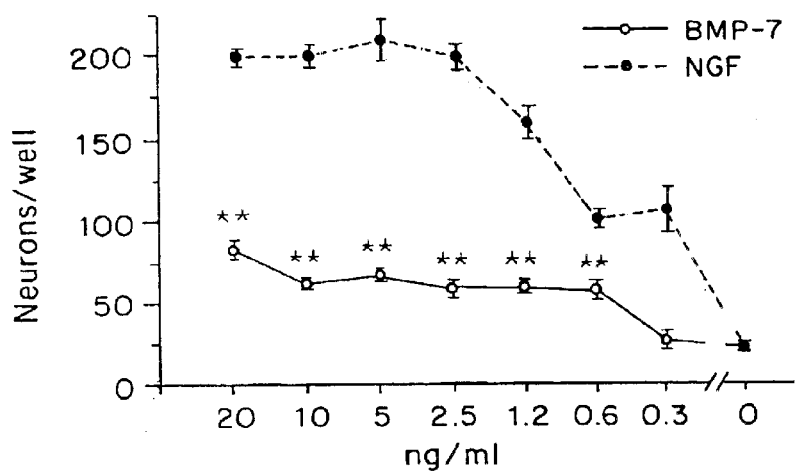
Figure 2E:
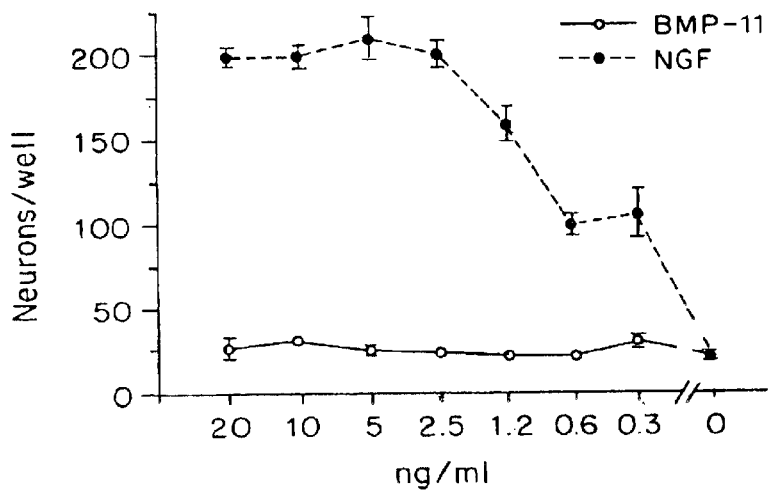
Figure 2F:
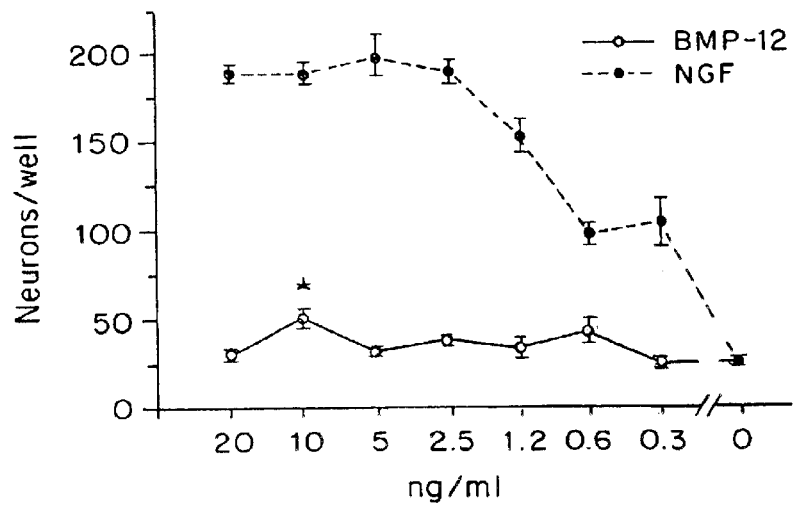

A description of preferred embodiments of the invention follows. The following examples illustrate the invention:
1. Synergistic Effect Between GDF-5 and BMP, Respectively, with NT-3 or NGF Dissociated cultures of embryonic chicken dorsal root ganglia (DRG) were generated as described in details by Krieglstein and Unsicker (Neurochem. Res., 21(7) (1996) 843–850). Briefly, DRGs from white Leghorn chick embryos (day 8) were dissected in $Ca^{2+}$-$Mg^{2+}$ free Hanks' balanced salt solution. After incubation in 0.08% trypsin for 15 min ganglia were dissociated by trituration. Cells were seeded in polyomithin-laminin coated 96-well microtiter plates (A/2 Costar) at a density of 1,200 cells/well. Growth factors were applied at the time of plating in a final volume of 50 ml Dulbecco's Modified Eagle's Medium supplemented with 0.25% bovine serum albumin, N1 additives and 100 U/ml penicillin. As a positive control, nerve growth factor (NGF) was used at the saturating concentration of 5 ng/ml. After 48 h of incubation at 37° C. in a humidified atmosphere containing 5% CO2, cultures were fixed with 2.5% glutaraldehyde. Neuronal cells were identified by their phase-bright and neurite-bearing morphologies and counted within 30% of the total surface area using phase contrast microscopy. In the first set of experiments we tested the survival promoting effect of several growth factors of the bone morphogenetic protein family. Dose-response analysis of GDF-5 and BMP, respectively, utilizing a wide range of serial dilutions, revealed that GDF-5 and all BMPs examined increased the number of surviving sensory neurons in a dose-dependent, saturable manner but at different magnitude (FIGS. 1 and 2). For example, GDF-5 can induce an approximately two-fold increase (at a saturating concentration of 20 ng/ml) in neuronal cell numbers, corresponding to about 20% of the NGF effect (FIG. 1). BMP-4 and BMP-7 showed approximately 35% of the maximal NGF effect (FIG. 2B and D, respectively), and BMP-2, -6, -11 and -12 had also a significant effect (FIG. 2A, C, E and F, respectively).

Figure 3:
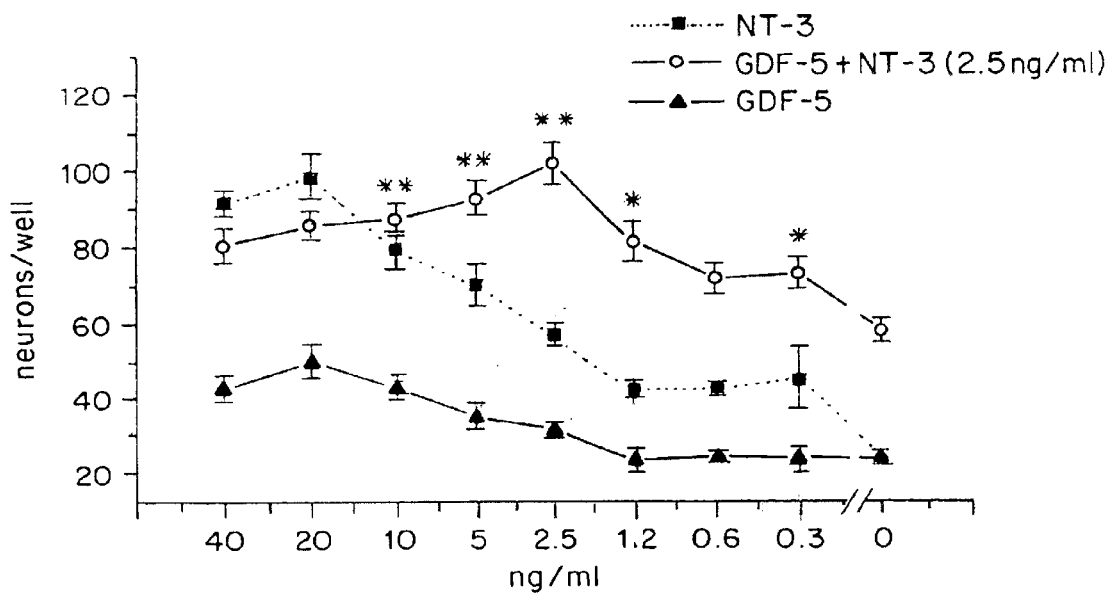
FIG. 3 depicts the co-treatment of E8 DRG neurons for 48 hours with GDF-5 at a serial dilution range and NT-3 at a constant concentration of 2.5 ng/ml (-'-). For comparison serial dilutions of GDF-5 (-▲-) as well as NT-3 ( . . . ■ . . . ) are given. Surviving neurons were counted in triplicate determinations of at least two independent experiments. Values given are means+SEM. Significance was derived from the comparison between neuronal numbers after GDF-5 plus NT-3 (2.5 ng/ml) and the individual factors. *P<0.05; **P<0.01.

Neurotrophic factors have been postulated to act in a finely tuned concert and sequence in determining neuronal survival. As shown in FIG. 3, addition of 2.5 ng/ml NT-3 to various concentrations of GDF-5 significantly increased DRG neuron survival above the NT-3 level indicating that NT-3 and GDF-5 can act synergistically. When added at saturating concentrations the two factors failed to increase neuronal numbers significantly above the levels of each single factor. This indicates that GDF-5 and NT-3 affect identical or largely overlapping neuron populations. In contrast, addition of GDF-5 (20 ng/ml) to NGF (5 ng/ml) significantly increased neuronal cell numbers above values obtained for each single factor (FIG. 3). This indicates that GDF-5 and NGF can promote different neuronal populations in our DRG culture system.

Figure 4:
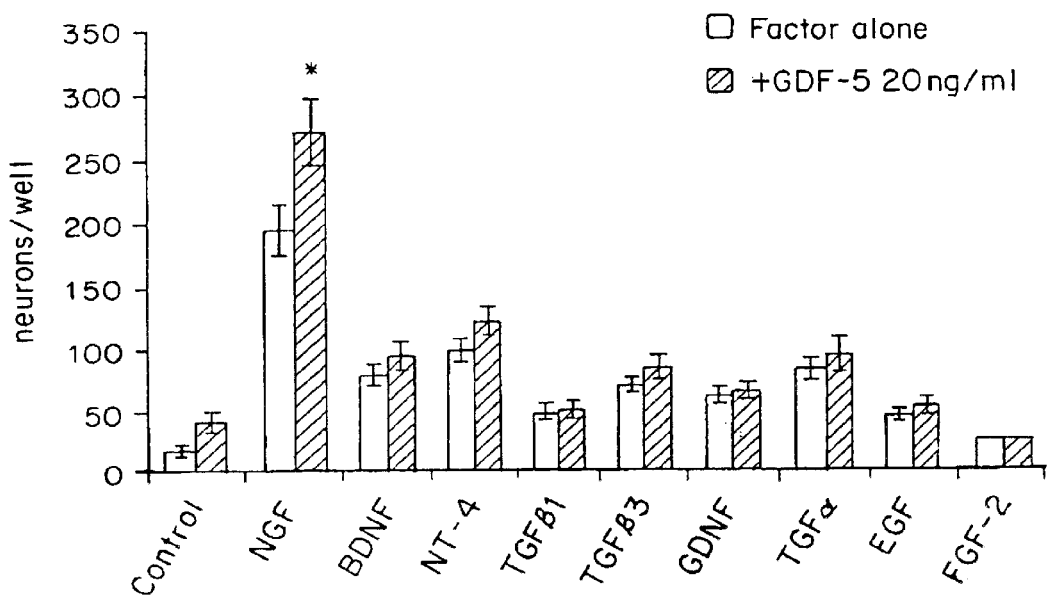
FIG. 4 depicts the survival of E8 DRG neurons cultured for 48 hours in the presence of various trophic factors at saturating concentrations with or without the addition of GDF-5 at a constant concentration of 20 ng/ml. Values represent the means+SEM of at least two independent experiments with triplicate determinations. *P<0.05 significant difference from neuronal numbers treated with NGF alone.

All other growth factors examined [brain-derived neurotrophic factor, BDNF; neurotrophin-4, NT-4; TGF-β1 and -β3, GDNF, epidermal growth factor, EGF; transforming growth factor-a, TGF-α; fibroblast growth factor-2, FGF-2] show also synergistic or additive effects when added together with GDF-5 at any tested concentrations (FIG. 4).

Figure 5A:
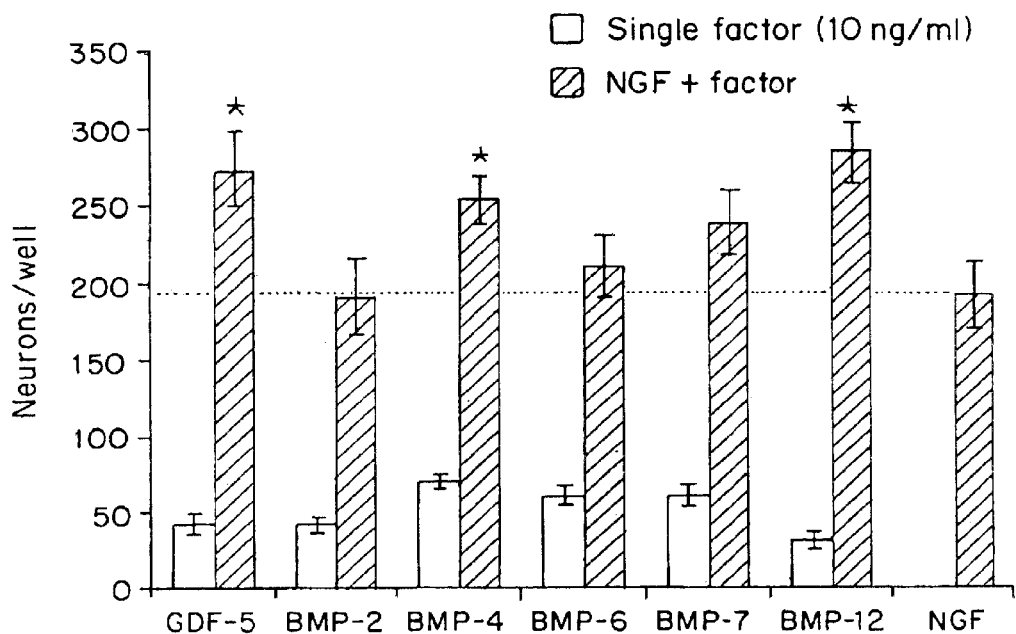
FIGS. 5A–5B depict the survival of E8 chick DRG neurons cultured for 48 hours in the presence of saturating conentrations of (5A) NGF (10 ng/ml) or (5B) NT-3 (10 ng/ml) applied seperately or in combination with the indicated BMPs. Cultures were treated for 48 h. Values given are mean+SEM of quadruplicate determinations of at least two independent experiments. *P<0.05 significant difference from neuronal numbers treated with NGF or NT-3 alone.
Figure 5B:
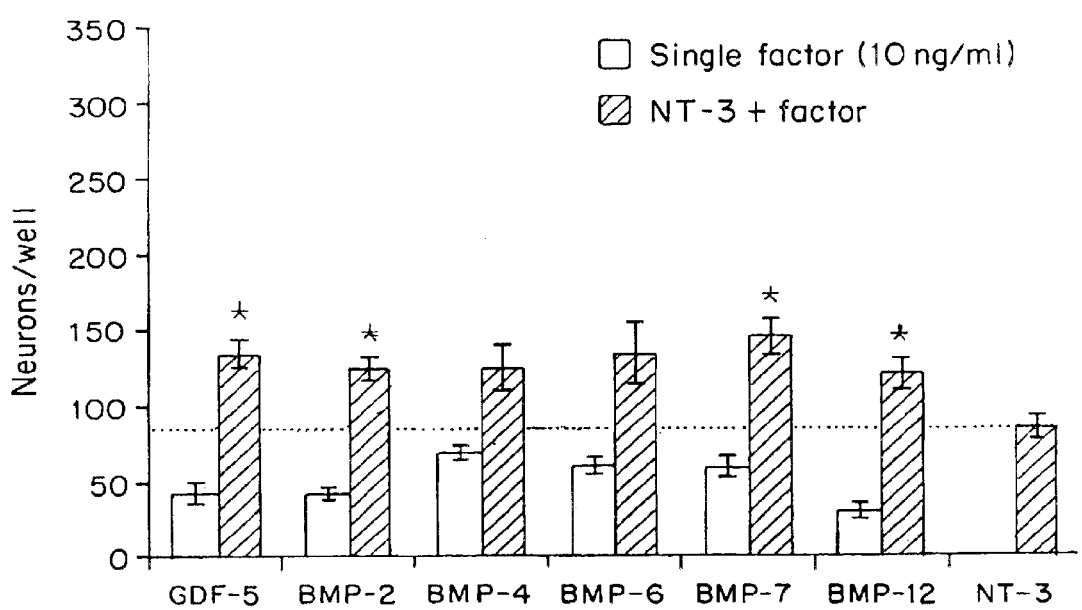

As shown in FIG. 5A, NGF in combination with GDF-5, BMP-4, or BMP-12 significantly increased survival of DRG neurons beyond levels maintained by the single factors. GDF-5 and BMP-12 promoted the survival of a very small neuron population when added alone. However, when combined with NGF, the increase in cell numbers was significantly higher than could be explained by simple addition. Therefore, these data indicate that GDF-5 and BMP-12 potentiate the NGF effect. The combination of BMP-4 with NGF show also significant effects. FIG. 5B documents that the promoting effects of GDF-5 and BMPs are also significant for NT-3. GDF-5, BMP-2, -7 and -12 significantly augmented the promoting effect of NT-3. In the case of GDF-5 and these BMPs together with NT-3 the results show that they promote the survival of largely none-overlapping neuron popultions. Combined treatments with BMPs and BDNF, NT-4, or GDNF indicate that these factors promote survival of largely overlapping neuron populations.

The present data demonstrate a survival promoting effect of GDF-5 and BMPs on a population of peripheral sensory neurons adding to the evidence that multifunctionality of GDF-5 and BMPs comprises a capacity as neurotrophic factors. Furthermore, GDF-5 and BMPs can synergistically affect survival of neurotrophin-supported DRG neurons. Additive effects of NGF and BMPs indicate that the BMP-supported DRG subpopulation comprises NT-3- or BDNF-dependent rather than NGF-dependent DRG neurons. DRG neurons with a requirement for NT-3 belong to the category of large sensory neurons mediating proprioceptive inputs from muscle to the spinal cord. BDNF-dependent sensory neurons comprise a probably heterogeneous population. Both populations may be putative targets for GDF-5 and BMPs consistent with their localization in the early developing limb. In the context of emerging evidence that TGF-βs can synergistically act with several neurotrophins the present data indicate that such a property can also be assigned to GDF-5 and BMPs. The present data are also consistent with the notion that GDF-5 and BMPs can significantly reduce doses of neurotrophins required for supporting sensory neurons. Neurotrophins are currently in clinical trial for several forms of peripheral neuropathies. Therefore, the pharmaceutical composition according to the present invention has a bearing on the application of neurotrophins, in particular in neuropathies responding to NT-3.

2. Synergistic Effect of TGF-β with Other Neurotrophic Factors and Neutrophins

The Neurotrophic Action of GDNF on Several Populations of Peripheral and CNS Neurons Essentially Requires TGF-β In Vitro and In Vivo.

GDNF has been proposed as a potent neurotrophic factor for cultured midbrain dopaminergic neurons, motoneurons, as well as peripheral autonomic and sensory neurons. All of the above culture systems share significant cellular complexity and/or the use of serum resulting in uncontrolled trophic conditions. A well-known constituent of almost every cell type as well as serum is TGF-β. For example, confluent cultures of B49 cells (from which GDNF was isolated), BHK, COS cells and 3T3 fibroblasts (which are frequently used for transfection experiments) secrete within 24 h 0.2 to 0.4 ng/ml TGF-β into their culture medium, as determined by its biological activity. Different batches of fetal calf and horse sera contain varying, but significant amounts of TGF-β (0.1–0.2 ng/ml in culture media with 10% serum).

Figure 6A:
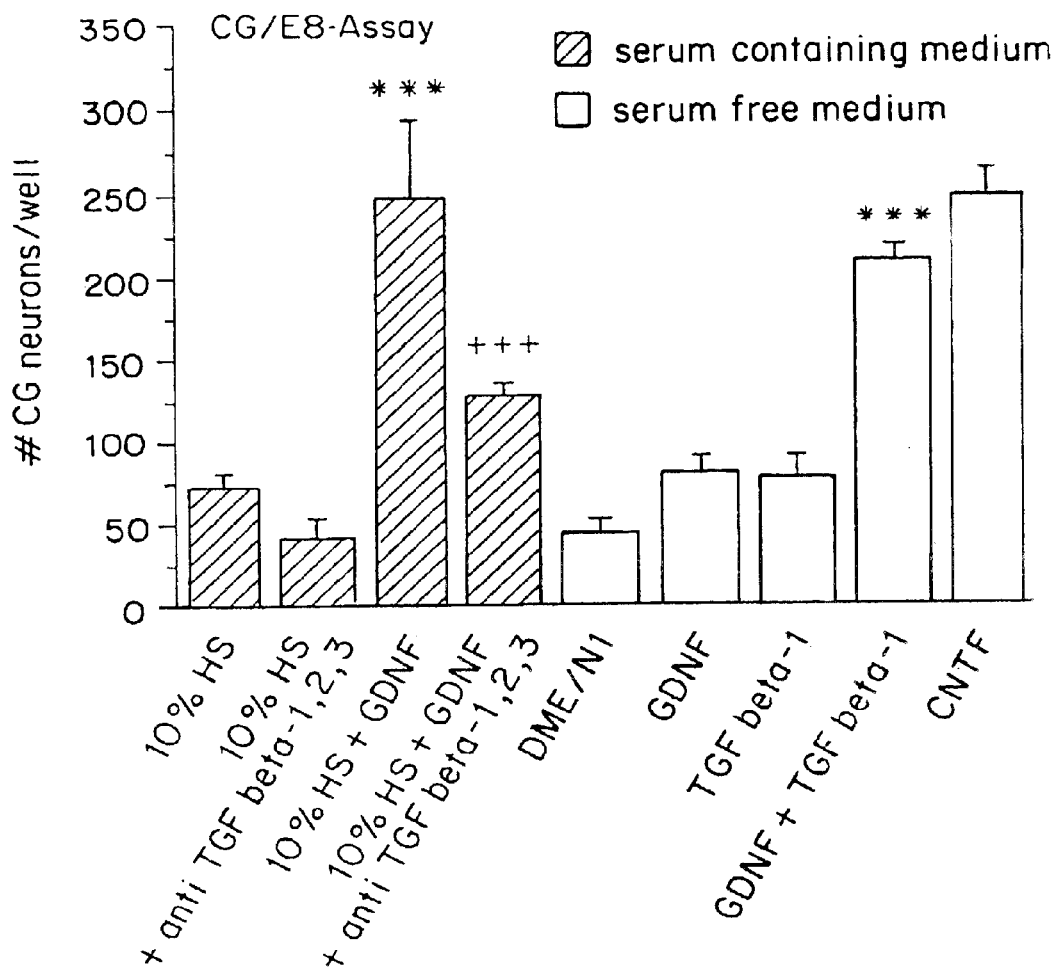
FIGS. 6A–6D depict the survival of peripheral autonomic and sensor neurons by the synergistic action of GDNF and TGF-$\beta$. 6A, chick ciliary ganglionic (CG) neurons; 6B, dose-response curve for the combined action of GDNF and TGF-$\beta$; 6C, chick dorsal root ganglionic (DRG) neurons; 6D, chick sympathetic ganglionic (SG) neurons. Neurons from the respective ganglia were isolated at embryonic day 8 (E8) and grown under the indicated conditions. Neurons were maintained in serum containing medium (grey bars; 6A, 6C, 6D) or in serum free medium (white bars: 6A, 6B, 6C, 6D). In the presence of 10% horse serum addition of a saturating concentration of GDNF promoted survival of each of the three neuron populations at levels identical to those achieved by addition of the respective neurotrophic factor (CNTF for CG, NGF for DRG and SG neurons) to serum-free culture media. Addition of a neutralizing antibody to TGF-$\beta$1, -$\beta$2, and -$\beta$3 reduced neuron survival to levels seen with the addition of serum alone indicating that GDNF required TGF-$\beta$ in the serum to achieve its survival promoting effect. In serum-free conditions, GDNF and TGF-$\beta$1, when added by themselves had virtually no survival promoting effect. However, when combined at optimal concentrations, both factors permitted neuron survival at levels identical to those achieved with the established neurotrophic factors CNTF and NGF, respectively.
Figure 6B:
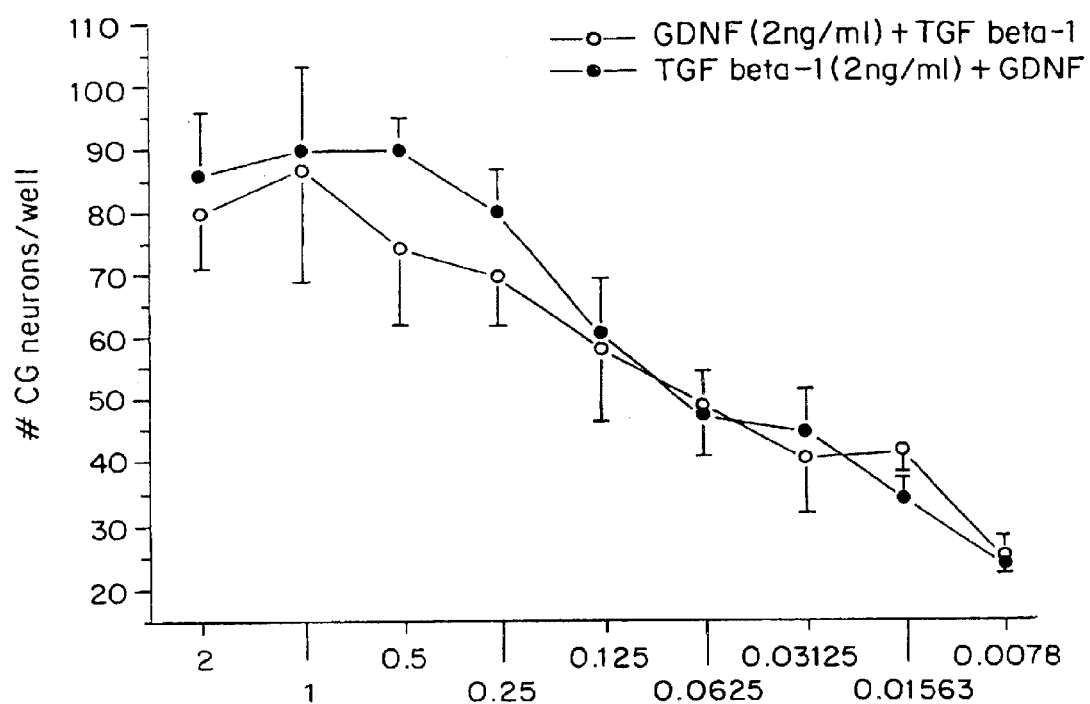

Using chick ciliary ganglionic neurons as an example, FIG. 6A demonstrates that GDNF supplemented with 10% horse serum maintains neurons over a 24 h period as effectively as a saturating concentration of CNTF (5 ng/ml). However, administering culture medium that had been pre-incubated with neutralizing antibodies to TGF-β (10 μg/ml, known to neutralize >95% of 1 ng/ml of TGF-β isoforms -β1, -β2, and -β3) significantly reduced the effect of GDNF showing that GDNF requires TGF-β for displaying its trophic effect. Consistent with this notion, switching from serum-containing to a fully-defined culture medium both GDNF and TGF-β (each at the saturating amount of 2 ng/ml) showed only marginal survival promoting effects. However, when combined the two factors promoted neurons as effectively as CNTF. In order to determine dose-response relationships required for the synergistic effect of GDNF and TGF-β each single factor at a concentration of 2 ng/ml was titrated in combination with serial dilutions of the other one. As shown in FIG. 6B 60 pg/ml of either factor combined with 2 ng/ml of the other factor represented the $EC_{50}$. The combination of 0.25 ng/ml and 2 ng/ml already elicited saturating effects. All isoforms of TGF-β (TGF-β1, -β2, and -β3) were consistently equipotent under the conditions used (not shown).

Figure 6C:
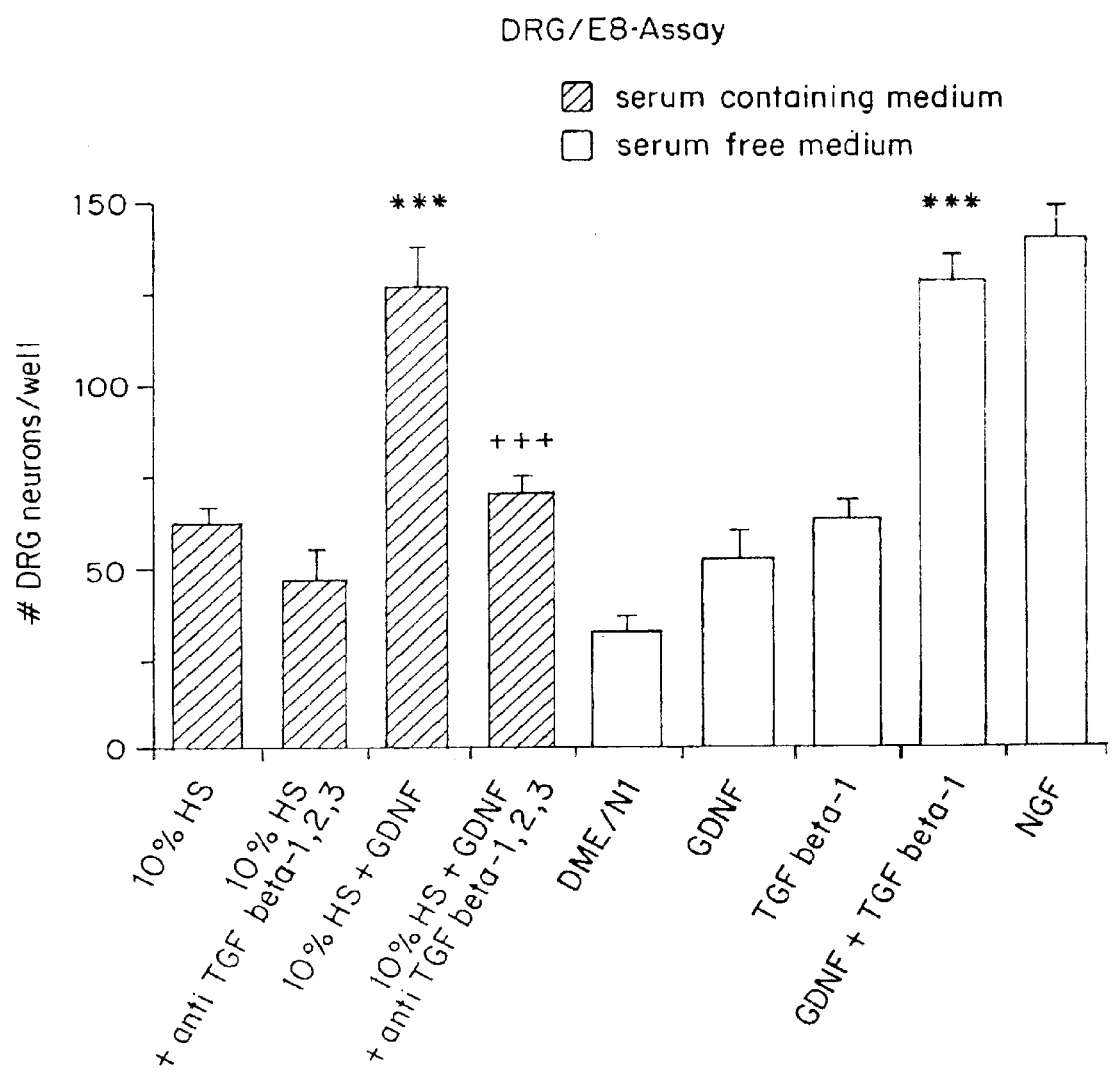
Figure 6D:
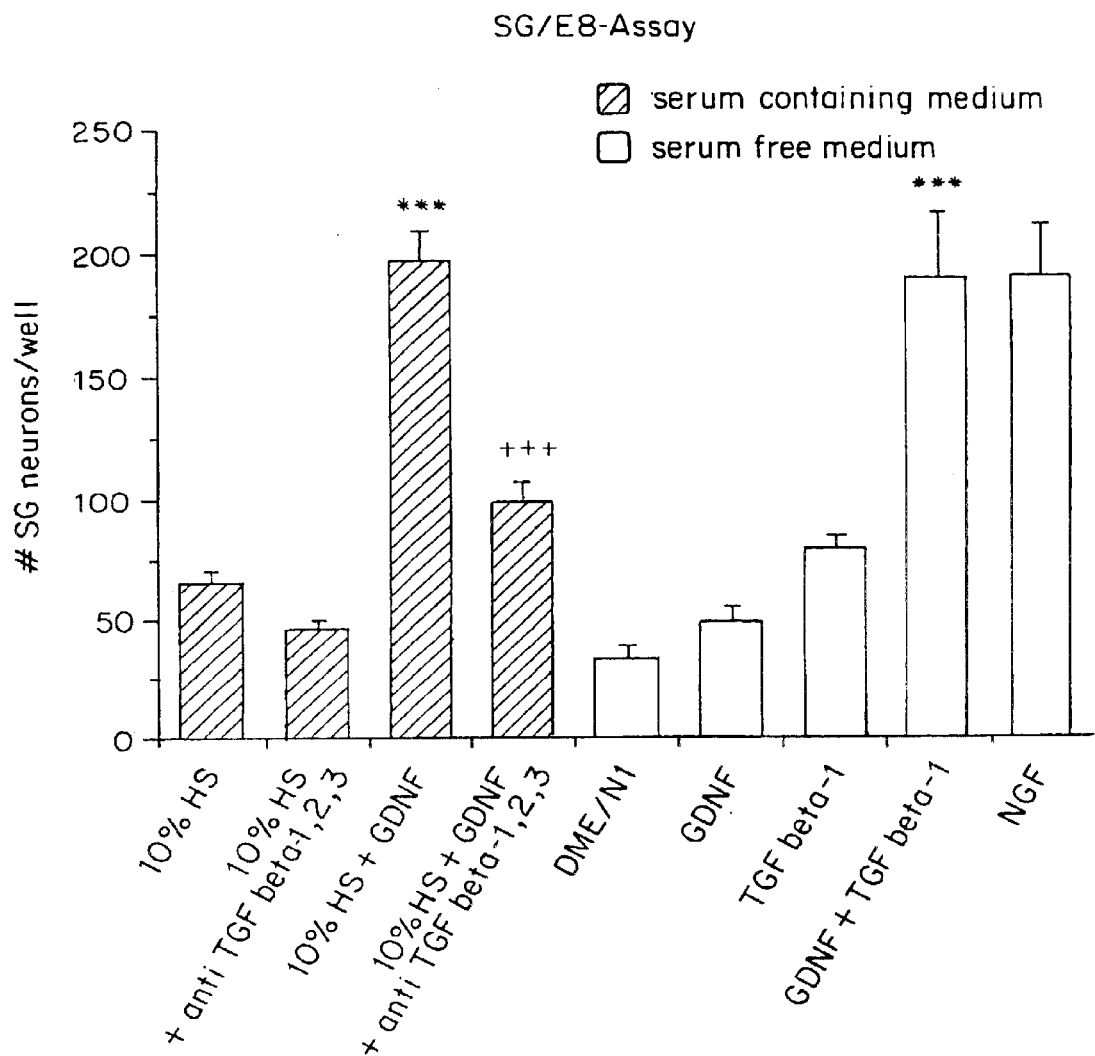
Figure 7A:
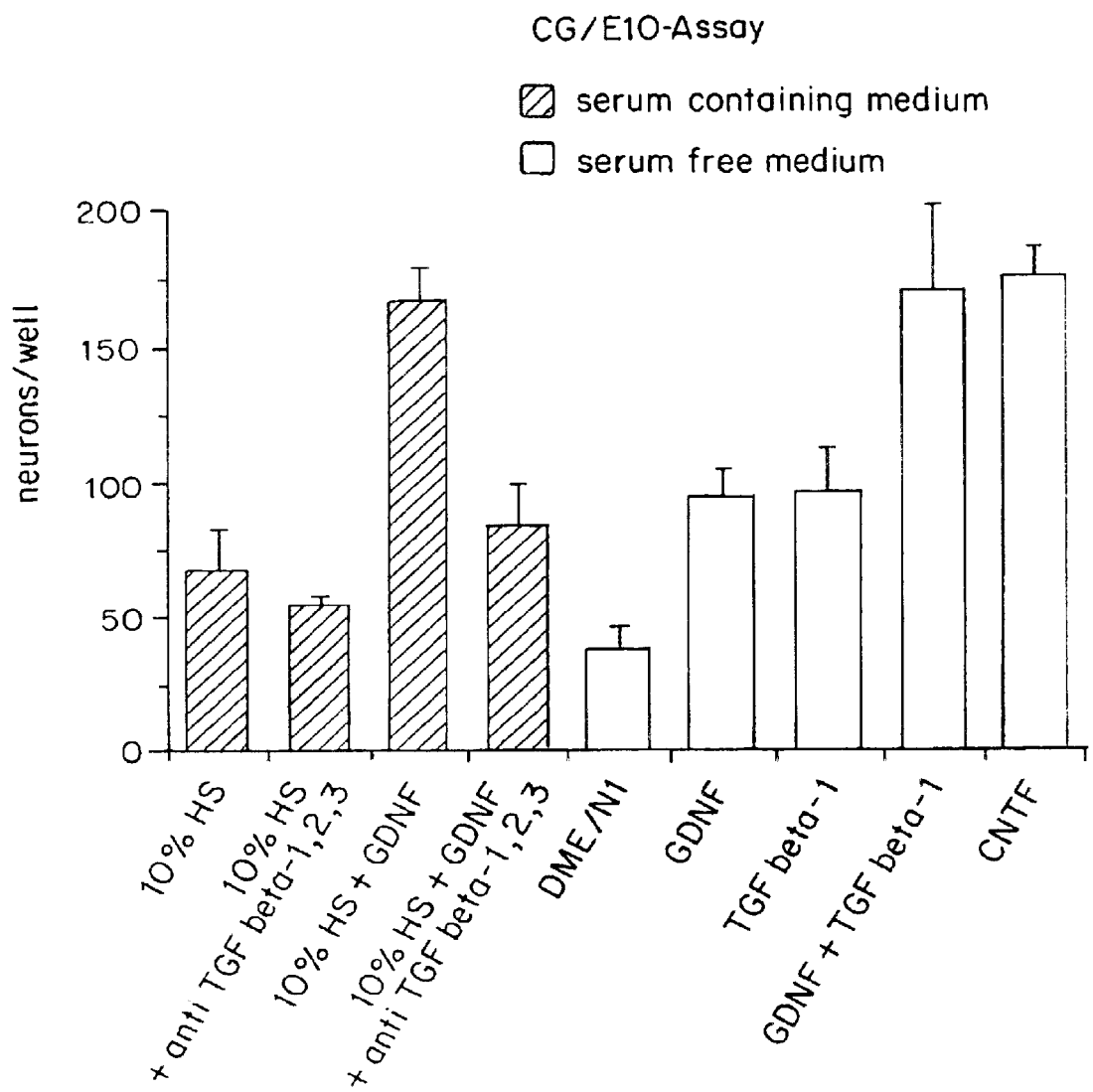
FIGS. 7A–7F depict an assay as performed in FIG. 1 using neurons from the respective ganglia of chick E10 (7A, 7B, 7C) and E12 (7D, 7E, 7F) embryos. Data indicate that the GDNF/TGF-$\beta$ synergism also applies to neurons at more advanced stages of development.
Figure 7B:
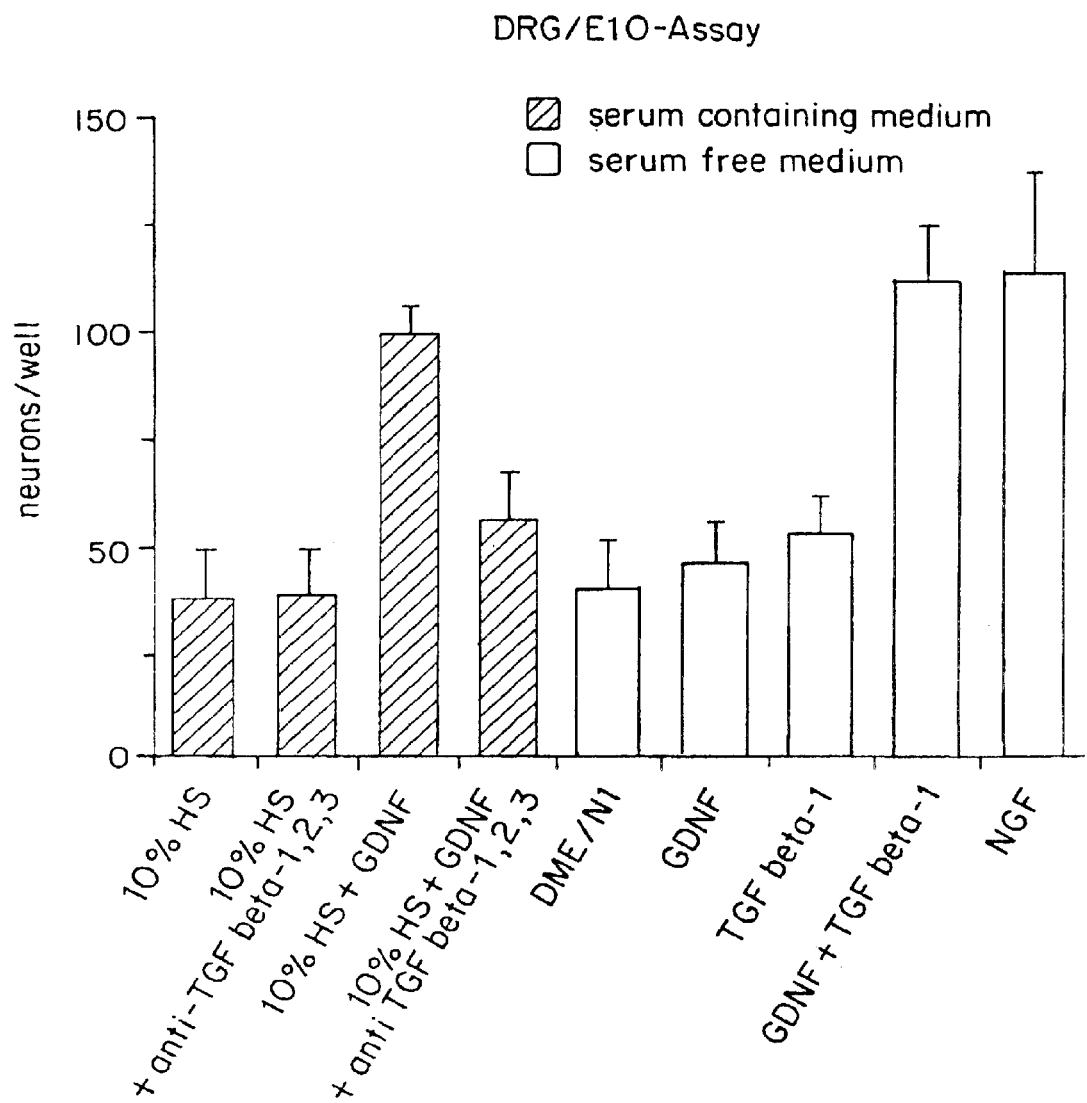
Figure 7C:
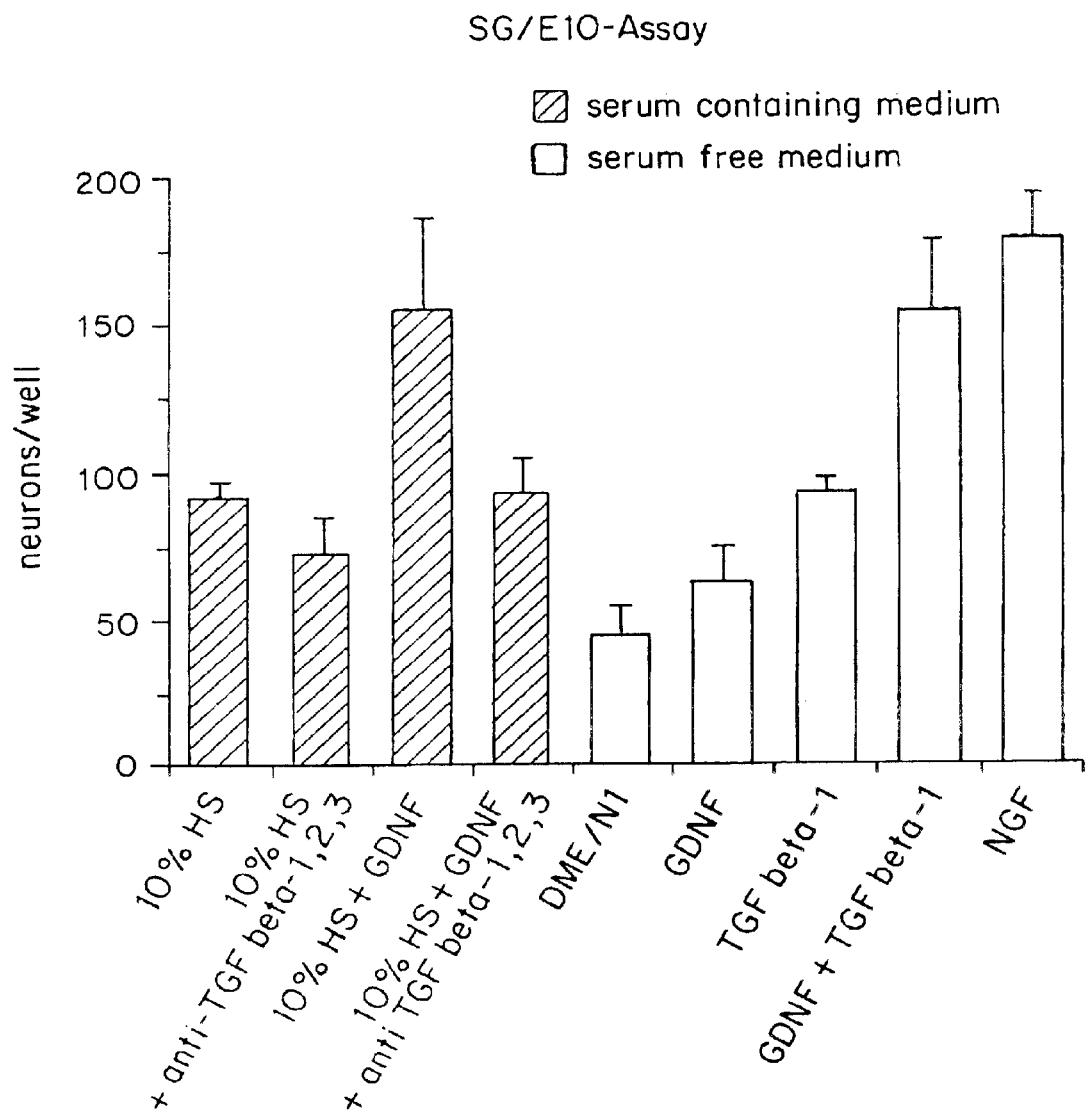
Figure 7D:
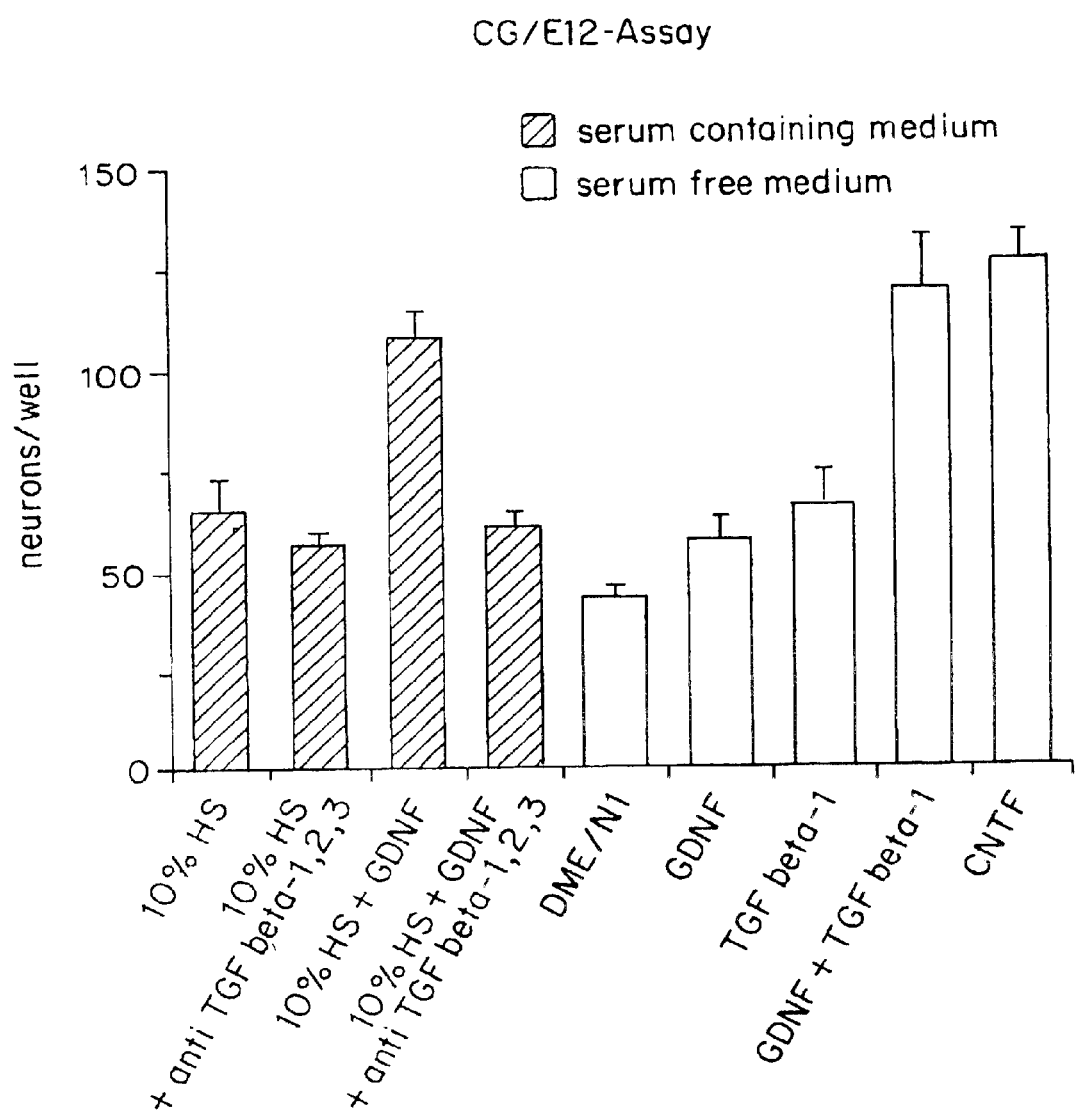
Figure 7E:
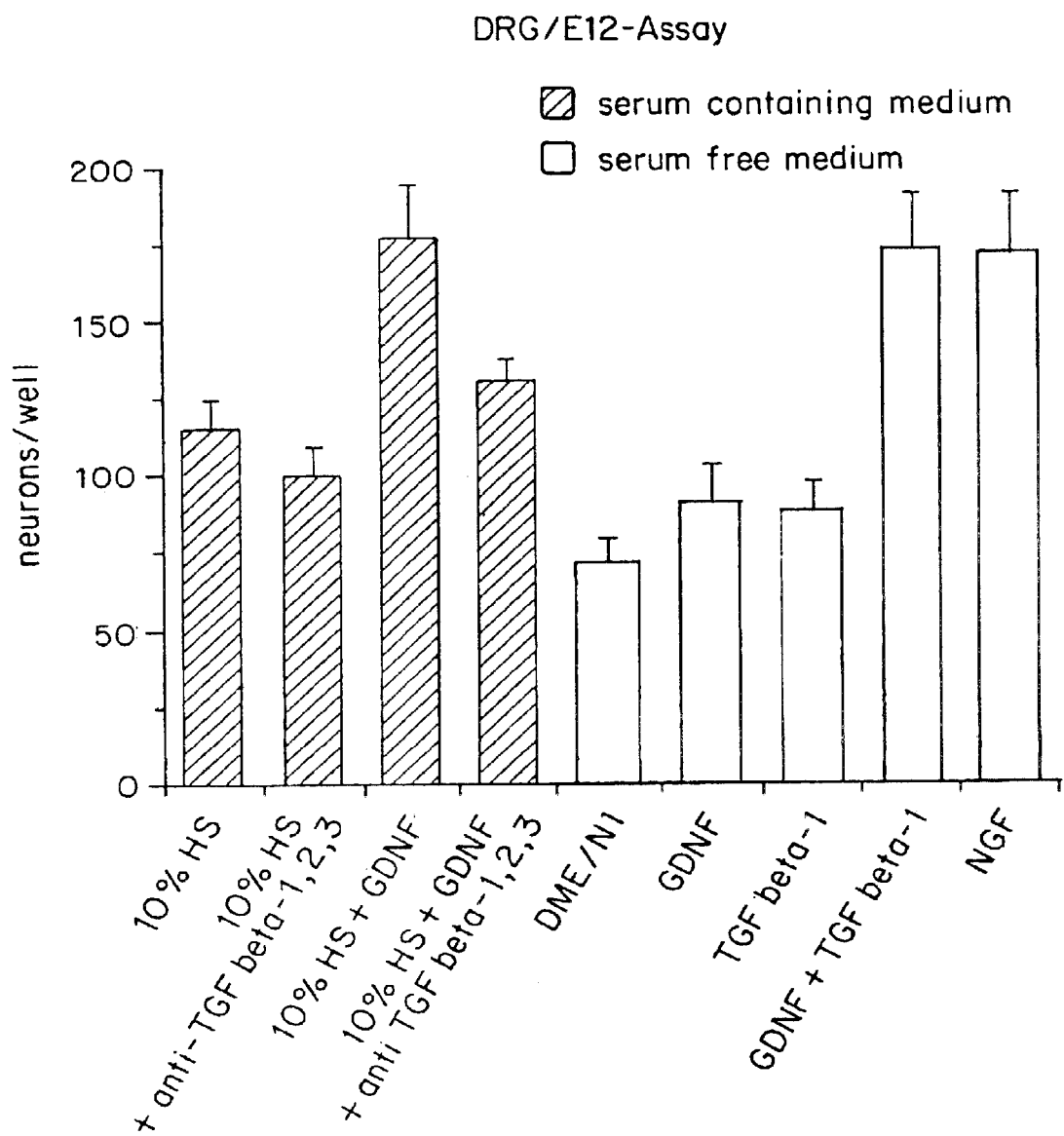
Figure 7F:
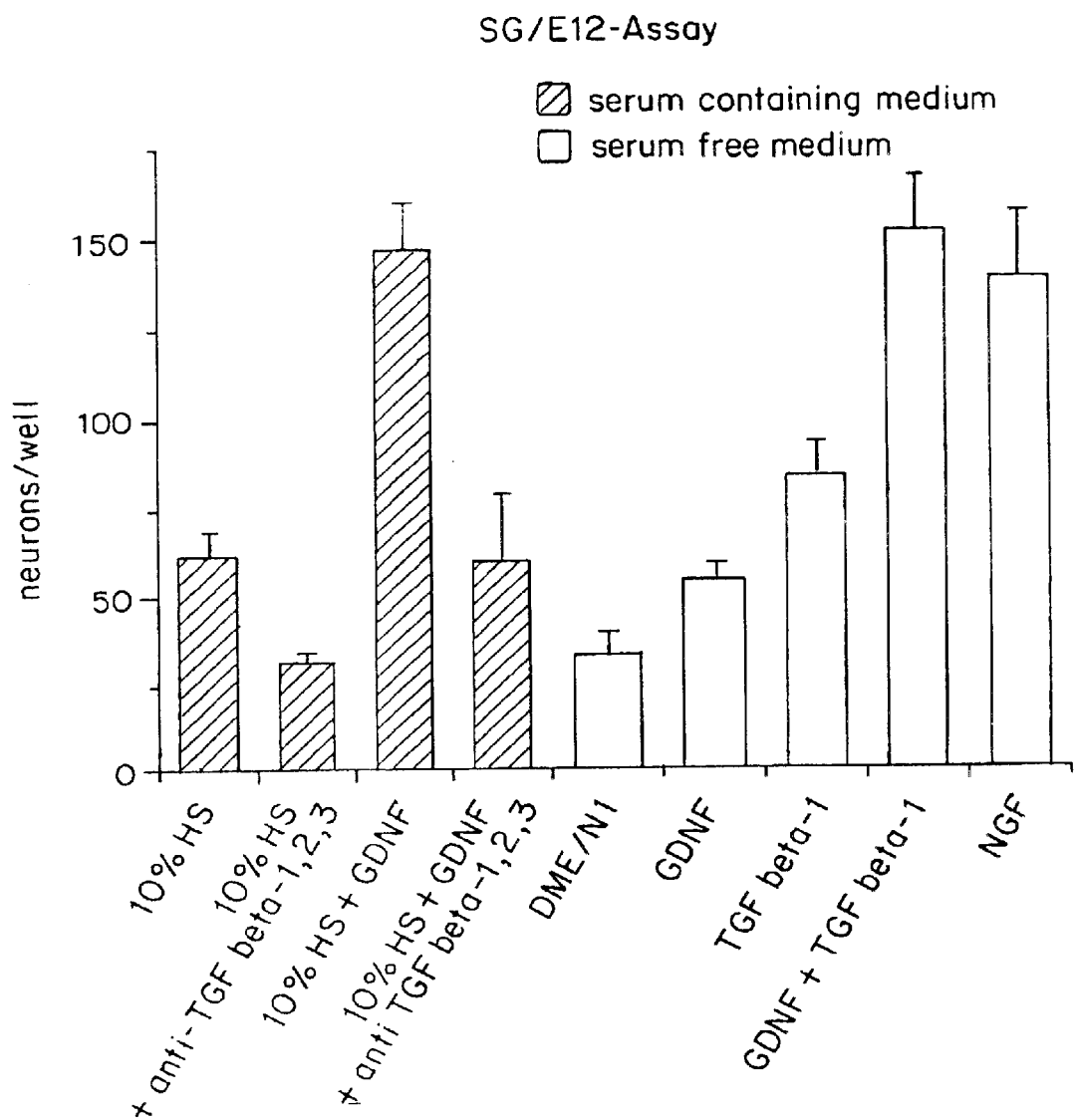

To investigate whether the synergistic effect of GDNF and TGF-β also applied to other populations of peripheral neurons, identical experiments were performed using chick sensory (DRG) and paravertebral sympathetic neurons isolated from embryonic day (E) 8 embryos. As shown in FIGS. 6C and 6D GDNF and TGF-β when co-administered to serum-free cultures maintained sensory and sympathetic neurons, respectively, as supported by a saturating concentration of NGF (5 ng/ml). Again, 10% horse serum substituted for TGF-β.

To exclude that the above effects are restricted to a brief developmental time window, the same set of experiments was performed on ciliary, sensory DRG and sympathetic neurons from E10 and E12 chick embryos. FIG. 7A–F shows that at all ages and on all neuron populations studied co-administration of GDNF and TGF-β mimicked the survival promoting effect of CNTF or NGF, respectively.

Figure 8:
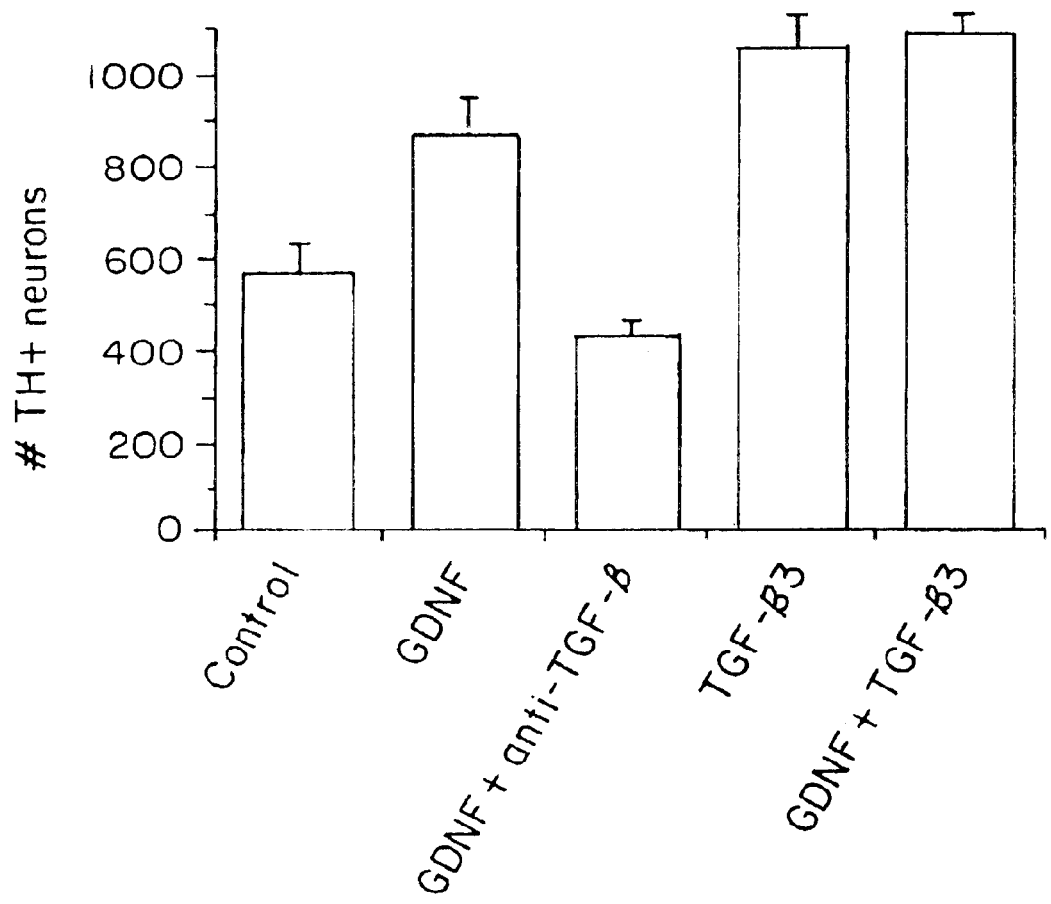
FIG. 8 depicts the survival promoting effect of GDNF on rat embryonic mesencephalic dopaminergic neurons (E14) is dependent on the presence of TGF-$\beta$. Dissociated cultures were treated with GDNF (10 ng/ml), with GDNF in the presence of anti-TGF-$\beta$1, -$\beta$2, -$\beta$3 (10 $\mu$g/ml), with TGF-$\beta$3 (2 ng/ml) or without any growth factor added (control) for 8 days in culture. Numbers of dopaminergic neurons were determined by counting the numbers of tyrosine hydroxylase (TH) immunoreactive neurons.

As shown in FIG. 8 GDNF and TGF-β each promoted the survival of dopaminergic neurons at 160% and 200%, respectively, of untreated control cultures.

Combinations of the factors did not further enhance survival consistent with the presence of endogenous TGF-β at an amount of approximately 0.2 ng/ml. Addition of neutralizing antibodies to TGF-β (10 μg/ml) abolished the trophic effect of GDNF. Accordingly TGF-β is required to permit GDNF exerting its neurotrophic potential on both peripheral and CNS neurons.

Figure 9D:
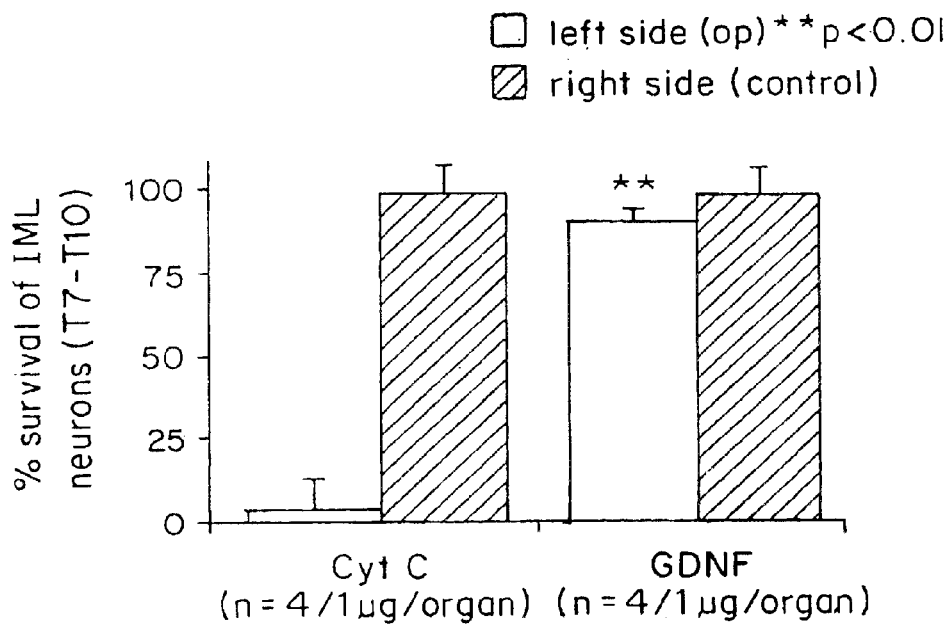
FIG. 9 depicts GDNF requires TGF-$\beta$ in vivo for establishing its neurotrophic effect. Retrogradely labeled preganglionic (IML) neurons to the adrenal medulla (a) express cRet (b) and GFR$\alpha$-1 (c) mRNAs. Cell death of the preganglionic neurons caused by adrenomedullectomy is fully prevented by substitution of GDNF into the adrenal cavity (d). Co-application of a neutralizing TGF-$\beta$ antibody significantly reduces neuroprotection by GDNF (e). LF, lateral funiculus of the spinal cord. Bar=100 $\mu$m.
Figure 9E:
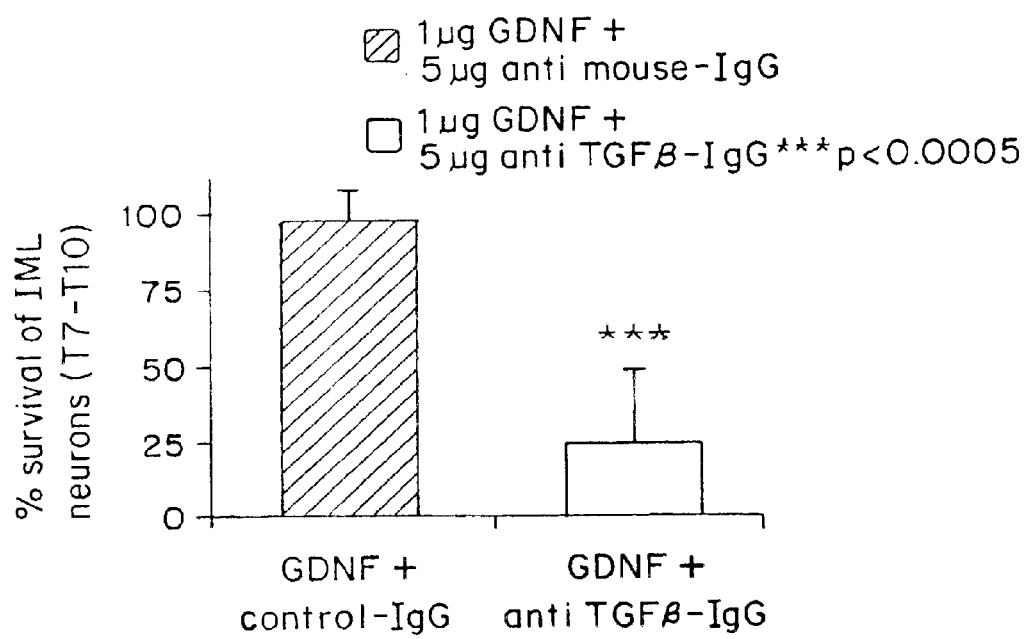

To prove that GDNF required TGF-β for establishing its neurotrophic activity in vivo, preganglionic neurons in the spinal cord of adult rats were deprived from their adrenal chromaffin target cells using unilateral surgical destruction of the rat adrenal medulla. This type of target deprivation causes the death of all preganglionic neurons to the adrenal medulla at four weeks, as previously shown by Blottner and Baumgarten (Exp. Neurol. 118 (1992) 35–46). As can be seen in FIG. 9a–c, preganglionic neurons express the GDNF receptors cRet and GFR-α1. FIG. 9d shows that the substitution of the target of the preganglionic neurons by administrating 1 μg GDNF in a piece of gelfoam to the medullectomized adrenal gland fully protected the neurons after four weeks. As shown in FIG. 9e, co-administration of TGF-β-neutralizing antibodies prevented the protective effect of GDNF. This shows that the presence of endogenous TGF-β is essential for permitting a neurotrophic effect of GDNF in vivo.

TGF-β Synergizes with GDNF by Stabilizing or Recruiting the GDNFR-α

Figure 10A:
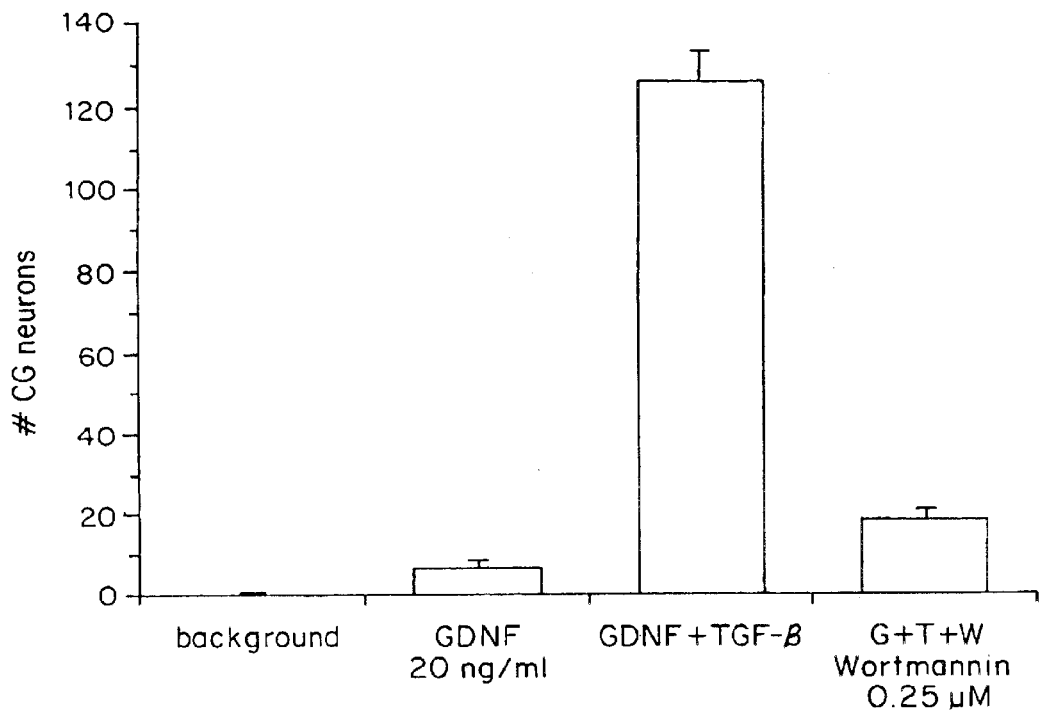
FIGS. 10A–10B depict the mechanisms underlying the synergistic actions of GDNF and TGF-$\beta$. (10A) Wortmannin, a specific inhibitor of IP3 kinase abolishes GDNF/TGF-$\beta$-mediated survival of chick ciliary ganglionic neurons indicating that IP3 kinase is an essential mediator in signal transduction of the combined action of GDNF and TGF-$\beta$. (10B) PIPLC, which liberates GPI-anchored cytokine receptors from the plasma membrane interferes, as expected, with the survival promoting effect of CNTF on chick ciliary ganglionic neurons, since CNTF employs a GPI-anchored alpha receptor for signal transduction. PIPLC does not interfere with the survival promoting effect of FGF-2, which does not employ an alpha receptor for signaling. Treatment of isolated ciliary neurons with PIPLC significantly reduces the survival promoting effect of GDNF and TGF-$\beta$ consistent with the essential role of a GPI-linked GDNF alpha receptor in GDNF signal transduction. Addition both, PIPLC and TGF-$\beta$ to isolated ciliary neurons, protects the GDNF alpha receptor indicating that the synergistic neurotrophic action of GDNF and TGF-$\beta$ may be due to a protective action of TGF-$\beta$ on the GDNF alpha receptor.

To begin to characterize details of the specific signal transduction pathway employed by GDNF to cooperate with TGF-β, further studies were carried out regarding the question whether activation of PI-3 kinase that has been shown as an early event in GDNF/c-ret-mediated signal transduction was involved. FIG. 10A shows that the specific PI-3 kinase inhibitor wortmannin at a concentration of 0.25 μM completely abolished the survival promoting effect of GDNF in conjunction with TGF-β on cultured ciliary neurons. Wortmannin did not interfere with the survival promoting effect of CNTF indicating that activation of PI-3 kinase is an essential event in mediating the survival promoting effect of GDNF/TGF-β, but not that of CNTF. Furthermore, this result indicates that wortmannin did not unspecifically compromise survival.

Figure 10B:
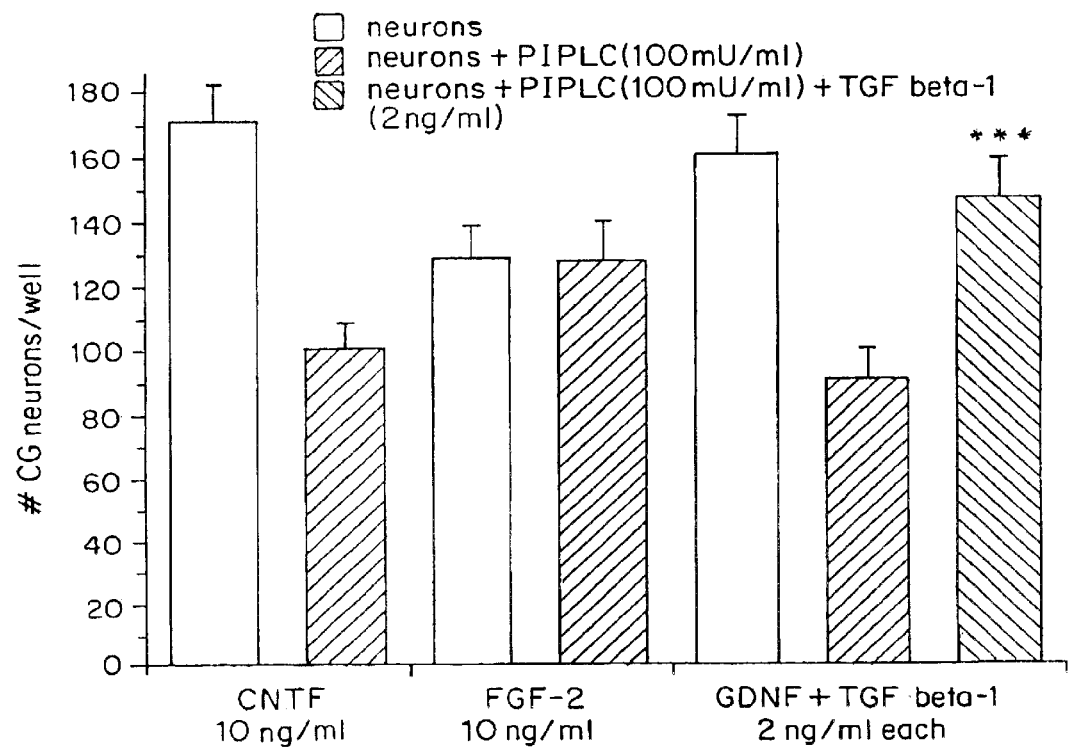
Figure 11:
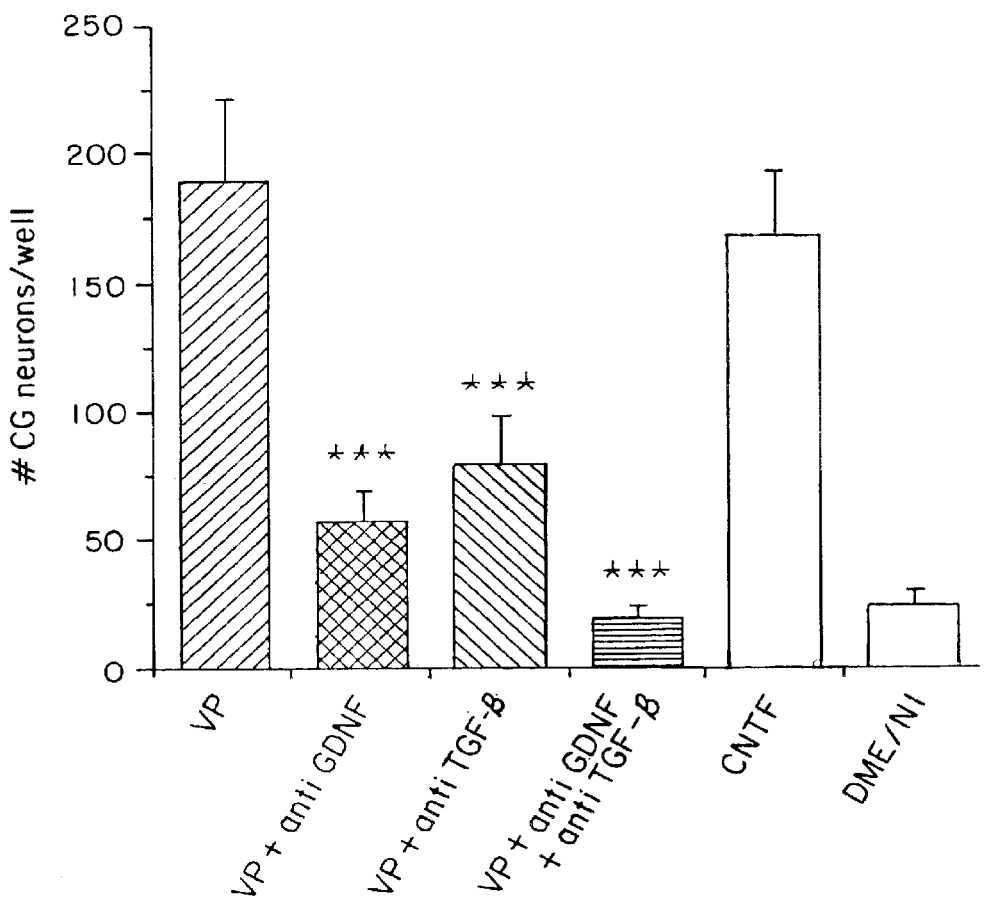
FIG. 11 depicts the the soluble proteins of chromaffin granules promote the survival of chick ciliary ganglionic neurons at a level identical to that achieved with a saturating concentration of CNTF (10 ng/ml). Addition of neutralizing antibodies to either GDNF (20 $\mu$g/ml) or the TGF-$\beta$s TGF-$\beta$1, -$\beta$2 and -$\beta$3 (10 $\mu$g/ml) significantly reduces the promoting effect of VP. Addition of both antibodies completely abolishes the neurotrophic effect of VP (0,5 ng/ml) indicating that GDNF and TGF-$\beta$ are the long-sought ciliary neurotrophic proteins contained in VP.

A further question was whether TGF-β might be involved in the stabilization and recruitment of the GPI-linked GDNFR-α. Phosphatidylinositol-specific phospholipase C (PIPLC) at a concentration of 0.1 U/ml was used to hydrolyse the GPI-achored receptors on dissociated ciliary neurons prior to plating. This procedure effectively reduced the survival promoting effect of CNTF (which utilizes a GPI-anchored GPARα), without affecting the survival promoting effect of FGF-2 (FIG. 10B). Hydrolysis of GPI-linked receptors significantly reduced the survival promoting effect of GDNF in its combination with TGF-β. However, when the PIPLC pretreatment was conducted in the presence of TGF-β (2 ng/ml TGF-β1) the survival promoting effect of GDNF was maintained (FIG. 10B). These data indicate an essential involvement of a GPI-linked receptor component in the neurotrophic effect of GDNF and a possible role of TGF-β in the stabilization and/or recruitment of the alpha receptor component.

Figure 12:
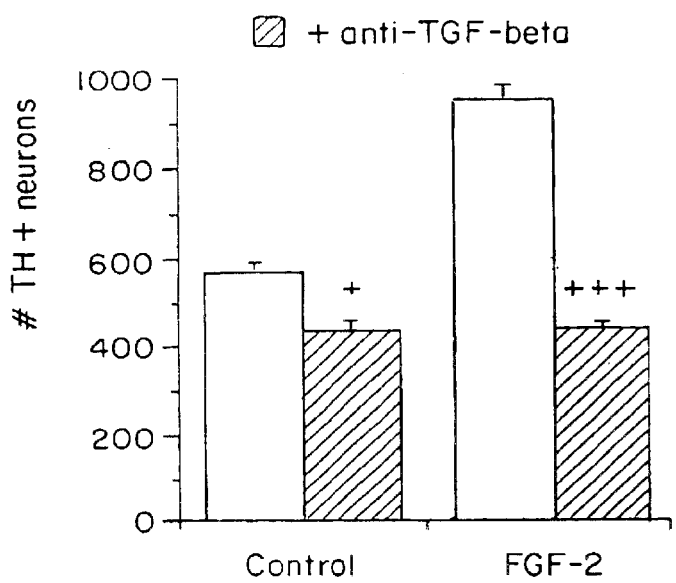
FIG. 12 depicts the ffect of neutralizing endogenous TGF-$\beta$ in mesencephalic neuron cul-tures. Numbers of surviving TH-immunoreactive neurons of mesencephalic cultures (E14/DIV8) after 8 days in culture treated with FGF-2 (10 ng/ml), medium only (control), in presence or absence of neutralizing antibodies to TGF-$\beta$1/-$\beta$2/-$\beta$3 (10 $\mu$g/ml). Data are given as mean±SEM (n=3), P-values are ***P<0.001 for increased survival as compared with control cultures and +P<0.05 or +++P<0.001 for decreased survival following antibody treatment.

TGF-β also Mediates the Neurotrophic Action of FGF-2. CNTF and Neurotrophins Fibroblast growth factor (FGF)-2 is known to act as a neurotrophic factor for dopaminergic neurons in the ventral midbrain. Earlier studies suggested that the neurotrophic effect exerted by FGF-2 is mainly indirect and mediated by mesencephalic ganglia (Engele and Bohn, J. Neurosci. 11 (1991) 3070–3078). As TGF-β is known to be a product of astroglial cells, it was tested whether TGF-β-neutralizing antibodies can abolish the neurotrophic effect of FGF-2 on cultured neurons derived from the embryonic midbrain floor. FIG. 12 shows that the treatment of the cultured neurons with FGF-2 (10 ng/ml) led to an 1.7 fold increase in survival of the cells compared to the negative control (medium alone). In contrast, addition of antibiodies specific for TGF-β1/-β2/-β3 completely abolished the survival promoting effect of FGF-2. These data show that the neurotrophic effect of FGF-2 on dopaminergic neurons in the ventral midbrain is mediated by TGF-β.

Figure 13A:
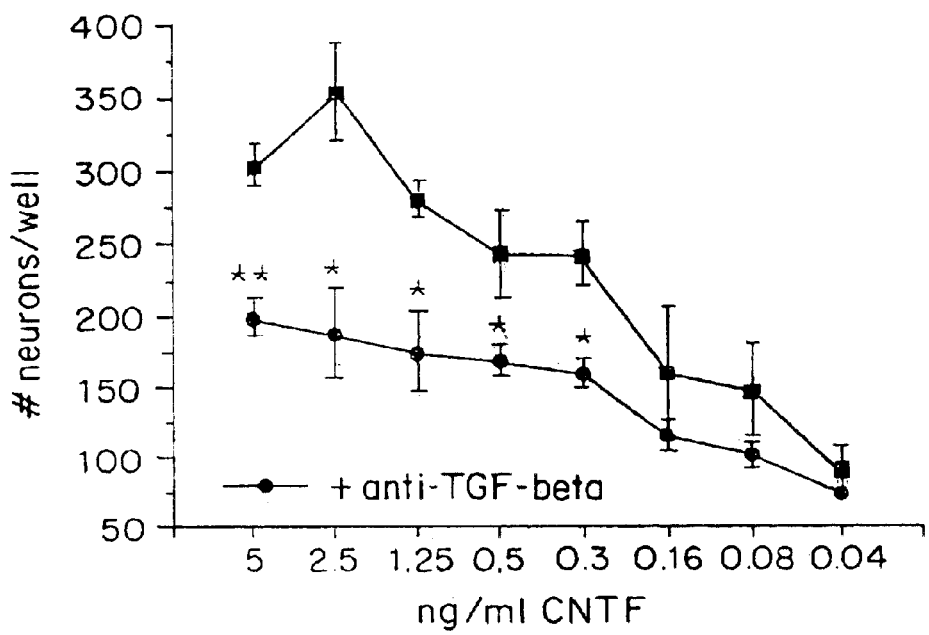
FIGS. 13A–13B depict the neutralizing endogenous TGF-$\beta$ reduces the survival promoting effects of CNTF and FGF-2 on chick CG neurons. Cultures were treated with CNTF (13A) or FGF-2 (13B) alone (-●-) at the indicated concentrations or in combination with neutralizing antibodies (-■-) to TGF-$\beta$1, -$\beta$2, -$\beta$3 (1 $\mu$g/ml). Data are given as mean±SEM (n=3). P-values are *P<0.05; **P<0.01 for decreased survival in the combination of growth factor plus anti-TGF-$\beta$ as compared to growth factor-treatment alone.
Figure 13B:
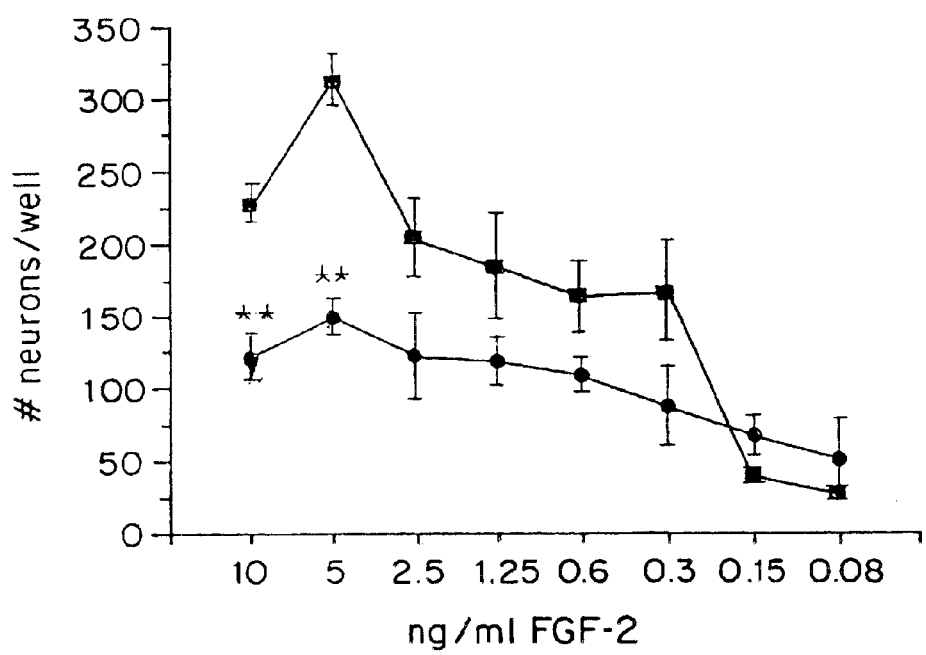

TGF-β was able to operate synergistically with FGF-2 and CNTF in the control of chick ciliary ganglion (CG) neuron survival. An antibody recognizing the TGF-β isoforms -β1/-β2/-β3 was employed to immunoneutralize TGF-β in cultures of CG neurons treated with CNTF or FGF-2, respectively (FIG. 13). Neutralization of TGF-β reduced CNTF- or FGF-2-mediated neuron survival by 40 to 60%. These data indicate that TGF-β released from cultured CG neurons synergistically acts with exogenous neurotrophic factors to assure neuron survival.

Figure 14A:
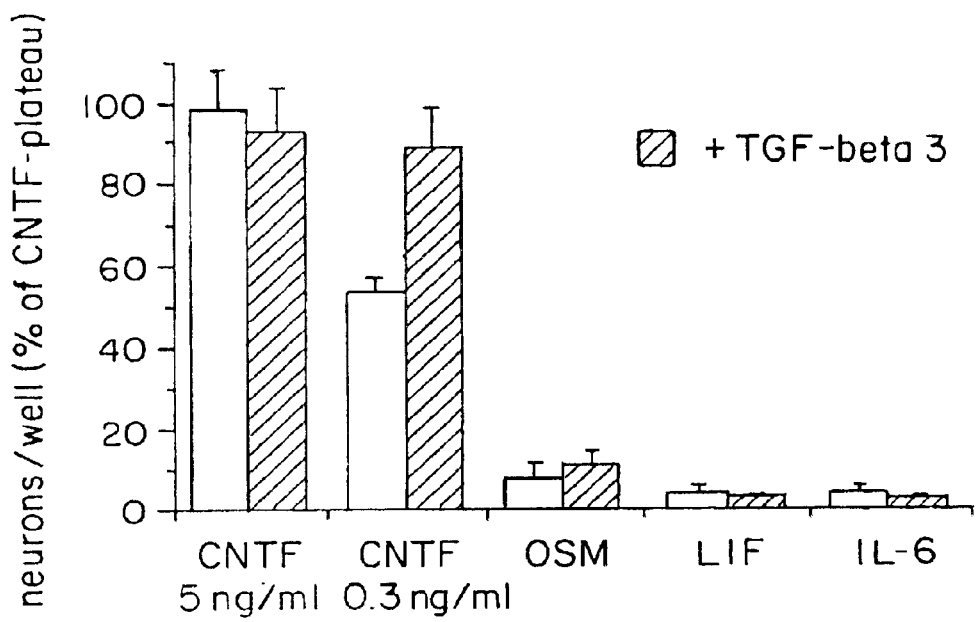
FIGS. 14A–14B depict TGF-$\beta$ induces responsiveness of chick CG neurons to CNTF, NGF and NT-3. Cultures were treated with (14A) CNTF (5 or 0.3 ng/ml), Oncostatin M, LIF, IL-6 (at 10 ng/ml), or (14B) NGF, NT-3, NT-4 in the absence or presence of TGF-$\beta$ (2.5 ng/ml). Data are given as percent of CNTF-plateau-survival as means±SEM (n=3). *P<0.05, **P<0.01 for increased survival in the combination with TGF-$\beta$3 as compared to the corresponding single factor treatment alone.
Figure 14B:
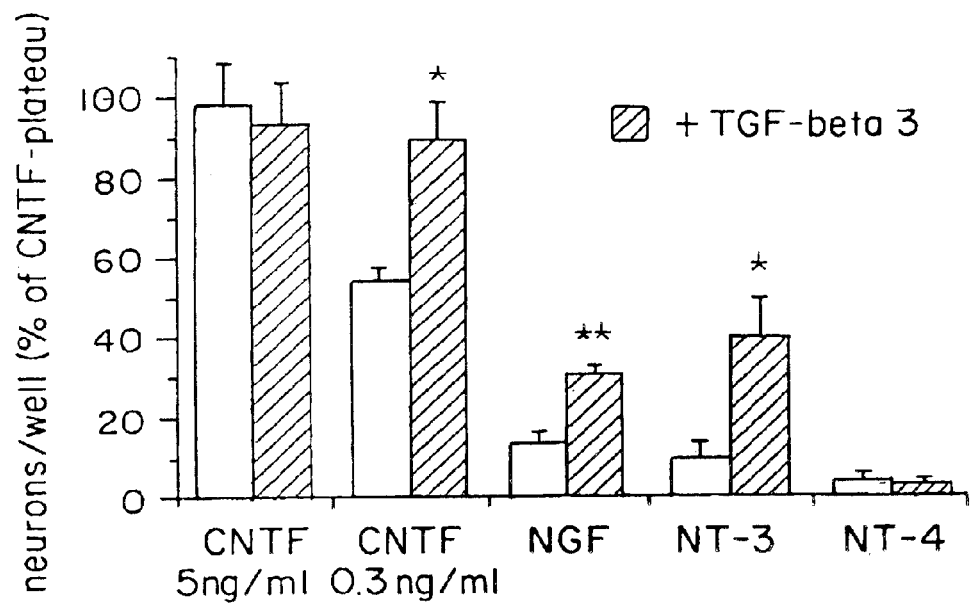

CNTF shares receptor and signal transduction components with members of a family of neuropoetic cytokines, which include leukemia inhibiting factor (LIF), oncostatin M (OSM), and interleukin-6 (IL-6) (Stahl and Yancopoulos, J. Neurobiol. 25 (1994) 1454–1466). As shown in FIG. 14A, TGF-β clearly augmented the efficacy of a non-saturating concentration of CNTF in terms of promoting CG neurons survival. OSM, LIF, and IL-6 did not support CG neurons, and further addition of TGF-β did not increase the effects of these cytokines beyond background levels. Neurotrophins are not established trophic factors for CG neurons (Collins, Brain Res. 467 (1988) 111–116). However, in combination with TGF-β, both NGF and NT-3 promoted survival at 35 to 40% of the CNTF-plateau (FIG. 14B). Although expression of trkA receptors, which permit signalling of NGF and NT-3 on CG neurons has not been shown as yet, the data presented indicate that TGF-β may cooperate neurotrophin receptor-mediated signalling on CG neurons.

Experimental Procedures

Materials

CMF: $Ca^{2+}/Mg^{2+}$-free Hanks' balanced salt solution, DMEM: Dulbeccos' modified Eagle's medium, and PSN were purchased from Gibco. Poly-L-ornithine, laminin, A23187, carbachol, and verapamil was purchased from Sigma, bovine scrum albumin (BSA) was from Serva (Heidelberg, Germany) and PIPLC from Boehringer Mannheim (Germany).

Horse serum (HS) was purchased from Gibco, fetal calf serum (FCS) batches 1 and 2 were from PAA, FCS batches 3 and 4 were from Euro and FCS batches 5 and 6 were from PAN.

Growth Factors

Growth factors were obtained from Boehringer Mannheim (NGF, 2.5 S NGF and recombinant human (rh) LIF), IC Chemikalien (recombinant rat (rr) CNTF, rh GDNF, rh Oncostatin M (OSM), rh IL-6, rh NT-3, rh NT-4 and rh BDNF) and Genetics Institute, Inc. (rh BMP-2, rh BMP-4, rh BMP-6, rh BMP-7, rh BMP-11 and rh BMP-12). For the experiments according to FIG. 5, GDF-5 was purchased form BIOPHARM, otherwise it was produced as described (Krieglstein et al., J. Neurosci. Res., 42(5) (1995) 724–732). Rh FGF-2 for the experiments according to FIG. 12 was obtained from Progen, and for all other experiments from IC Chemikalien. Lyophilized factors were resuspended in culture medium (see below) to give a final concentration of 1 μg/ml and stored in aliquots of 50–100 μl at −70° C. until use.

Antibodies

The neutralizing antibody to TGFβ-1,2,3 was purchased from Genzyme and to GDNF from Santa Cruz Biotechnology.

Agarose conjugated antibodies to TGFβ-1 and to GDNF were from Santa Cruz Biotechnology. The peroxidase conjugated α-rabbit antibody was purchased from Sigma.

Animals for Experiments According to FIGS. 1, 3, 4, 6, 7, 8 and 11

Fertilized white Leghorns chick eggs were obtained from a local aviary and incubated in a humidified egg chamber at 37.8° C.

Animals for Experiments According to FIGS. 2, 5 and 12–14

Fertilized white Leghorns chick eggs were obtained from a local aviary and incubated in a humidified egg chamber at 38° C. until E8.

Cell Culture for Experiments According to FIGS. 1, 3, 4, 6, 7, 8 and 11

Assays of Neurotrophic Activity:

Embryonic chick ciliary (CG), dorsal root (DRG), and sympathetic (SG) ganglia at embryonic day(s) (E) 8, 10, and 12, were dissected, freed from nerve roots and connective tissue and collected in CME. Ganglia were incubated in trypsin (ICN), washed and dissociated by trituration using fire-polished Pasteur pipettes. Cultures were set up in 96-well microtiter plates (Costar, A/2), precoated with poly-L-ornithine and laminin at a density of 1,200–1,500 cells/well in DMEM supplemented with N1 additives, 0.25% BSA, and 0.1% PSN (DME/N1) and incubated at 37° C. in a 5% $CO_2$ incubator.

At appropriate times (CG: 24 h, DRG: 48 h, SG: 72 h) cultures were fixed by addition of 2.5% glutardialdehyde in phosphate buffered saline (PBS). Numbers of surviving neurons were determined by direct counting of 30% of the surface area using phase contrast microscopy.

Treatment with PIPLC:

Phosphatidylinositol-specific phospholipase C (PIPLC) is an enzyme that specifically cleaves glycosyl-phosphatidylinositol (GPI) linkages. Embryonic chick ciliary ganglionic neurons (E8) were isolated and seeded as described before. Neurons were incubated for 1 h at 37° C. with 1) 100 mU PIPLC or II) 100 mU PIPLC+2 ng/ml TGFβ or III) without enzyme and then growth factors were added. The number of surviving neurons was determined 24 h later.

Preparation of Chromaffin Cells and Release Studies:

The isolation of bovine adrenal medullary chromaffin cells was performed by collagenase digestion and Percoll gradient centrifugation essentially as described by Unsicker et al. (Neuroscience 5 (1980) 1445–1460). Chromaffin cells were seeded into 25 $cm^2$ plastic culture flasks (Falcon) at densities of $1 \times 10^6$ cells/ml and routinely had a purity of at least 90–95%. The culture medium consisted of DME/N1 and for stimulation experiments, the culture medium was replaced after 30 h with prewarmed stimulation buffer containing I) carbachol (100 μM) or II) carbachol (100 μM) plus verapamil (10 μM) or III) the Calcium ionophore A23187 (2 μM) or IV) no additives and incubated for 15 min at 37° C. After collection of the stimulation buffer an aliquot for determination of catecholamines by HPLC (Müller et al., J. Neurosci. Methods 4 (1981) pages 39–52) was removed, and the remainder was prepared for protein analysis.

Cell Lines:

The cell lines B49, 3T3 and COS were grown in 10% FCS/DMEM with 1% PSN and the cell line BHK was set up in DMEM/F 12 with 5% FCS and 1% PSN in plastic culture flasks.

Conditioned medium of these different cell lines was collected and aliquots were stored at −80° C. and then prepared for MLEC-bioassay to determine TGFβ activity.

Proteins from Bovine Chromaffin Granules

The isolation of bovine chromaffin granules was according to the protocol by Winkler et al. (Handbook of Physiology, Section 7, Vol. 6, pp. 321–339). Granules were lysed by a freeze-thaw cycle in a 10 mM phosphate buffer (pH 7.2) and the soluble proteins were separated from membranes by ultracentrifugation at 100,000 g for 30 min. The supernatant then was dialyzed overnight against 10 mM phosphate buffer, pH 7.2 by using membrane tubing (Spectropor) with a 3.5 kDa cutoff. Aliquots were stored at −80° C.

Agarose Conjugate/Western Blots

To 1 ml of the stimulation buffer with or without additives from chromaffin cells 10 μl of the antibody agarose conjugate were added and incubated at 4° C. overnight with mixing. The pellet was washed with PBS and then resuspended in 50 μl of electrophoresis sample buffer and boiled for 2 minutes. Samples were separated by electrophoresis on a 12.5% SDS-PAA gel and transferred to nitrocellulose membrane (Hybond, Amersham). The nitrocellulose membrane was blocked with 3% low fat milk powder/0.1% BSA in Tris buffered saline (TBS, pH 7.3), incubated with primary antibody (1:200 in 0.1% BSA/TBS) overnight at 4° C. followed by peroxidase conjugated secondary antibody (1:2000 in 0.1% BSA/TBS). Finally the membrane was developed using the Amersham enhanced chemiluminescence (ECL) detection system.

Assay for TGF-β's

Determination of TGF-β activity was performed by using the mink lung epithelial cell (MLEC) (kindly provided by Dr. Rifkin, New York University, New York, USA) bioassay (Abe et al., Anal. Biochem. 216 (1994) 276–284). Transfected MLEC cultures were set up in a 96-well microtiter plate (Costar) at a density of $1.6 \times 10^4$ cells/well in DMEM (high glucose) with 10% FCS and geneticin (250 μg/ml) and allowed to attach for 3 h at 37°C. in a 5% $CO_2$ incubator. The medium was then replaced with 100μl of test sample in DME/N1 (activated with HCl) and incubated overnight at 37° C. in a 5% $CO_2$ incubator. Cells were washed twice with PBS and lysed by using 100 μl of lysis buffer (Promega) for 2–3 h at RT. To determine TGFβ activity, 80 μl of the lysates were transferred to a test tube and analyzed using a Luminometer (Lumat, Berthold/Germany) by 100 μl injections of luciferase reagent (Promega). Luciferase activity was reported as relative light units (RLU) and all assays were performed in triplicate.

Statistics.

Statistical comparisons were made with one-way ANOVA, included in the MicroCalOrigin software. Differences were considered statistically significant at * $P<0.05$, $P<0.005$, and * $P<0.0005$.

Cell culture for Experiments According to FIGS. 2, 5 and 12–14

Dissociated cultures of embryonic chicken dorsal root ganglia (DRGs) were generated as described in details by Krieglstein and Unsicker (Dev. Brain. Rees. 93 (1996) 10–17). Briefly, DRGs were dissected in $Ca^{2+}$-$Mg^{2+}$ free Hank's balanced salt solution (CMF). After incubation in 0.08% trypsin (BioWhittaker) for 15 min, ganglia were dissociated by gentle trituration using fire-polished Pasteur pipettes. Cells in suspension (neuron/non-neuron ratio 1:2) were seeded in polyomithin-laminin coated 96-well microtiter plates (A/2 Costar) at a density of 1,200 cells/well. Growth factors were applied at the time of plating in a final volume of 50 μl Dulbecco's Modified Eagle's Medium supplemented with 0.25% bovine serum albumin, N1 additives (Bottenstein et al., Exp. Cell Res. 125 (1980) 183–190) and 100 U/ml penicillin. As a positive control, nerve growth factor (NGF) was used at the saturating concentration of 10 ng/ml. After 48 h of incubation at 37° C. in a humidified atmosphere containing 5% $CO_2$, cultures were fixed with 2.5% glutaraldehyde in phosphate buffered saline (PBS). Neuronal cells were identified by their phase-bright and neurite-bearing morphologies and counted within 30% of the total surface area using phase contrast microscopy. All experiments were performed in at least triplicate in two independent experiments. Data are presented as mean±SEM. Statistical comparisons were made with student's double t-test, ANOVA and MicrocalOrigin software. Differences were considered statistically significant at *$P<0.05$, $P<0.01$, $P<0.001$.

Assay for Preganglionic Neuron Protection In Vivo

Adrenomedullectomy was performed on adult male Hanover-Wistar rats. Preganglionic neurons in the spinal cord innervating adrenal medullary chomaffin cells were identified by retrograde tracing with Fast Blue or Fluoro-Gold (FG). Factors (1 μg each) were soaked in gelfoam (Spongostan, Ferrosan, Soeburg, Denmark) prior to implantation into unilaterally medullectomized adrenal glands. Numbers of FG-labeled preganglionic neurons were determined by cell counts of complete series of longitudinal sections through spinal cord segments T7–T10 four weeks post-surgery. Only brightly fluorescent neurons containing a clearly visible nucleus were counted. Total numbers were corrected for possible double counts of split nuclei according to Abercombie's formula. Numbers of preganglionic neurons to the adrenal medulla surviving in sham-operated animals and on the unlesioned side were set as 100%. Data are given as mean values±SEM and the statistical significance of intergroup differences was determined by Student's t-test.

In Situ Hybridization

In situ hybridizations were performed on paraffin sections of the thoracic spinal cord essentially as described in Arumae et al. (J. Cell Biol. 122 (1993) 1053–1065). Probes were derived from rat GFRα-1, nucleotides 294–1039, and mouse cRet, nucleotides 2534–3217. After hybridization, all sections were dipped and exposed for 2–3 weeks, counterstained with haematoxylin, air dried and embedded in DPX. No hybridization signal was detected with the probes on sense orientation.

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition having a synergistic neurotrophic activity consisting of GDNF and TGF-β.

2. A composition having a synergistic neurotrophic activity, consisting of GDNF and TGF-β, and further comprising a pharmaceutically acceptable carrier.

3. A composition having a synergistic neurotrophic activity consisting essentially of GDNF and TGF-β.

* * * * *